United States Patent [19]
Szostak et al.

[11] Patent Number: 5,688,670
[45] Date of Patent: Nov. 18, 1997

[54] SELF-MODIFYING RNA MOLECULES AND METHODS OF MAKING

[75] Inventors: Jack W. Szostak, Boston; Jon R. Lorsch, Cambridge, both of Mass.; Charles Wilson, Bonny Doon, Calif.

[73] Assignee: The General Hospital Corporation, Boston, Mass.

[21] Appl. No.: 299,498

[22] Filed: Sep. 1, 1994

[51] Int. Cl.$^6$ .......................... C12P 19/34; C07H 21/02; C12Q 1/68

[52] U.S. Cl. ........................ 435/91.21; 435/6; 435/172.1; 536/23.1

[58] Field of Search .......................... 435/91.2, 91.21, 435/91.31, 194, 6, 172.1; 536/23.1, 23.2

[56] References Cited

U.S. PATENT DOCUMENTS

| | | | |
|---|---|---|---|
| 4,987,071 | 1/1991 | Cech et al. | 435/91.31 |
| 5,037,746 | 8/1991 | Cech et al. | 435/91.31 |
| 5,093,246 | 3/1992 | Cech et al. | 435/6 |
| 5,116,742 | 5/1992 | Cech et al. | 435/91.31 |
| 5,180,818 | 1/1993 | Cech et al. | 536/23.1 |
| 5,270,163 | 12/1993 | Gold et al. | 435/6 |

OTHER PUBLICATIONS

"Concise Encyclopedia Chemistry" Walter de Gruyter, New York. pp. 185–190 & 372–374 1994.

Cech, Science 236:1532–1539 (1987).

Huizenga et al., Biochemistry 34:656–665 (1995).

Szostak, Trends in Biochemical Sciences 17(3):89–93 (1992).

Wilson et al., Nature 374:777–782 (1995).

International Search Report, PCT/US95/10813, dated 20 Dec. 1995.

Bartel et al. "HIV–1 Rev Regulation Involves Recognition of Non–Watson–Crick Base Pairs in Viral RNA", Cell, 67(3):529–536, (1991).

Bartel et al., "Isolation of New Ribozymes from a Large Pool of Random Sequences", Science, 261:1411–1418 (1993).

Beaudry et al., "Directed Evolution of an RNA Enzyme", Science, 257:635–641 (1992).

Benner et al., "Modern metabolism as a palimpsest of the RNA world", Proc. Natl. Acad. Sci. USA, 86(18):7054–7058, (1989).

Bock et al., "Selection of single–stranded DNA molecules that bind and inhibit human thrombin", Nature 355(6):564–566, (1992).

Connell et al., "Three Small Riboligonucleotides with Specific Arginine Sites", Biochemistry, 32(21):5498–5502, (1993).

Ellington et al., "Selection in vitro of single–stranded DNA molecules that fold into specific ligand–binding structures", Nature, 355:850–852, (1992).

Ellington et al., "In vitro selection of RNA molecules that bind specific ligands", Nature, 346:818–822, (1990).

Famulok, "Molecular Recognition of Amino Acids by RNA–Aptamers: An L–Citrulline Binding RNA Motif and Its Evolution into an L–Arginine Binder", J. Am. Chem. Soc., 116:1698–1706, (1994).

Famulok et al., "Stereospecific Recognition of Tryptophan Agarose by in Vitro Selected RNA", J. Am. Chem. Soc., 114:3990–3991, (1992).

Gibbons, "Molecular Scissors: RNA Enzymes Go Commercial", Research News, p. 521, Feb. 1, 1991.

Green et al., "Selection of a Ribozyme that Functions as a Superior Template in a Self–Copying Reaction", Science, 258:1910–1915, (1992).

Jenison et al., "High–Resolution Molecular Discrimination by RNA", Science, 263:1425–1428, (1994).

Joyce, "RNA evolution and the origins of life", Nature 338:217–224, (1989).

Lehman et al., "Evolution in vitro of an RNA enzyme with altered metal dependence", Nature 361:182–185, (1993).

Lorsch et al., "In Vitro Selection of RNA Aptamers Specific for Cyanocobalamin", Biochemistry, 33(4):973–982, (1994).

Pan et al., "In vitro Selection of RNAs that Undergo Autolytic Cleavage with $Pb^{2+}$", Biochemistry, 31(16):3887–3895, (1992).

Sassanfar et al., "An RNA motif that binds ATP", Nature, 364:550–553, (1993).

Tsai et al., "In vitro selection of an RNA epitope immunologically cross-reactive with a peptide", Proc. Natl. Acad. Sci. USA, 89:8864–8868, (1992).

Tuerk et al, "Systematic Evolution of Ligands by Exponential Enrichment: RNA Ligands to Bacteriophage T4 DNA Polymerase", Science, 249:505–510, (1990).

Wilson et al., "Ribozyme Catalysis", Current Opinion in Structural Biology, 2:749–756, (1992).

*Primary Examiner*—John LeGuyader
*Assistant Examiner*—Thomas G. Larson
*Attorney, Agent, or Firm*—Clark & Elbing LLP

[57] ABSTRACT

The invention concerns a method for creating, identifying, and isolating ribozymes capable of binding a selected ligand and catalyzing a reaction involving the selected ligand. The method entails sequential selections for ligand binding molecules and catalytic molecules. The invention also includes novel ribozymes produced by these methods.

19 Claims, 21 Drawing Sheets

SEQ ID NO: 4

CLASS I

```
22  TGATTCGCTAGCACGTCATTGGCTGGTAACACATGACACTTATACGAGCGAAAAACTACGGCA
45  AGTCTCGCTAGCACCTTATTGGCTGGTGGTAACACCTGACACTATACGAGCGAAAAAACTACGGCA
46  GGACTCACTAGCACGTTGTTGGCTGGTGGTAACACCCGACACCCTATACGACCGAAAAAACTACGGCA
57  AGACTCACTAGCGCGCGTTATTGGCTGTGGTAGCCCCCTGACACTATACGAGCGAAAATACTGCGGCA
    CCCTGGTCCGTTAGGGACAACGACTAAAGTTAGTGCCCACGGGCTCGTTCAAGTTGTCACGG  SEQ ID NO:6
    CTCTGGTCCGTCGTAGCGGTACGGCCATGGACTTAAGATAGTGCCCACGGGGCTCGTTCAAGTTGTCACGG  SEQ ID NO:7
    CTCTGGTCCATACGGACTTGGACTTGGACTAAAGTTAGTGCCCACGGGGCTCGTTCAAGTTGTCACGG  SEQ ID NO:8
    CCCTGGTCCGTACGGGACATGGACATATGTTAGTGCCCACGGGGCTCGTTCAAGTTGTCACGG  SEQ ID NO:9
              65   70   75   80   85   90   95  100  105  110  115  120  125
```

CLASS II

```
 4  GGATATGTTGATTCGCCCCCAGCCAGCCTATAAAGTGACTCAATTCGAGGGACGCAACTACGGCACCG
25  AGATGTGTCGATTCGCCACACAGCCAAACAAAGCGGCCCAATTCGAGGGACGACCAACTTCGGCACCG
43  AGATGTGTTGATTCGCCCCTCGGCCGTTCTGGCCCTGTTTAGTGACCAATTTCGAGGGACGACCAACTTCGGCACCG
    TCTATCTGAATCGAATGGACCGCGGAGTCGAGGTTGCCGTCTCTACTCTAACGTTAGCGGAAAACGTGGGTTGCG  SEQ ID NO:10
    TCTATCAGAGAACGGGACGCGGAGGTTCTAGTGCCGTCTCTATCCTAACGTTAGCGGAAAACGAGGGTTGCG  SEQ ID NO:11
    TCTACCTGCAATAGACGAGGTTACTTATGCAGGCCCTACTTTAACGTTAGCGGAAAACGAGGGTTGCG  SEQ ID NO:12
              65   70   75   80   85   90   95  100  105  110  115  120  125
```

CLASS III

```
          5        10        15        20        25        30        35        40        45        50        55        60
          |        |         |         |         |         |         |         |         |         |         |         |
 9'      AGTCTACATGGAAGTTGTACTATCTAAGTGTACTCACCAAAGACGAGGCAGGAAATACGGCA
16       AGGCCACTACTTAGATGTCGCACTATCTAAGCGTACACGCCAATTACGAGGGCAGGAAATACGGCA
44       AGACCTCGTGTAAGTCGTACTATCTAGGAGTGCACACGAAT-ACGAGGGCAGGAAATACGGCA
                                                                                                                    ▲
          65       70        75        80        85        90        95        100       105       110       115       120
          |        |         |         |         |         |         |         |         |         |         |         |
 9       CCATTGGCTACGCAAGGCCCAAGTGCCCGGCGTCGTTTCAGAAAGGATAACGTTAGCCTG    SEQ ID NO:13
16       CCTCCAGTCTACGCAAGGCCCCAGTGCCCTGCCTCAGTTCGGAACGGATAACGTTACCCTG  SEQ ID NO:14
44       CCATAA-CTACGCAAGGCCCAAGTGCCCGGCCTTGATTCAGAACGGATAACGTTAGCCTG    SEQ ID NO:15
                                                                   ▲
```

CLASS IV

```
          5        10        15        20        25        30        35        40        45        50        55        60        65
          |        |         |         |         |         |         |         |         |         |         |         |         |
10       TTATTTCGTTCGCACCCAGTGATCGCTCGGGACTGGGCCCTCCGCTAGGGAGGACATTGCGCACCC
14       AGAAGTTGTTCGCACCCAGTGAACGCTCGGGACTGAACGCTCCGCTAGGGAGGACATTGCGGCACCC
44       GGATATTGTTCGCACCCTGCACCCTGCGATCGCTTGGGACTGGGCCTCCGCTAGGGAGGACATTGCGGCACCC
                                                                                                                              ▲
          70       75        80        85        90        95        100       105       110       115       120       125       130       135
          |        |         |         |         |         |         |         |         |         |         |         |         |         |
10       AAACGACCACACAGAACGTGCTAACGATAGTGCCGGCTAGCATCCGTGAATGAACTGCTGCTGGCG  SEQ ID NO:16
14       GAACTATCACTCAGAACGTCAGAACGTGCTATCGTTGCTATAGCCGGCTAGCCGGCTGATTATGAACTGCTGCTGCTGGGCG  SEQ ID NO:17
44       AAACTATCACTCAGAACGTCAACGTGCTAACGATAGTGCCGGCTAGCTTTCTGTAAGTGAACTGCTGCTGCTGTTGGCG  SEQ ID NO:18
```

CLASS V

```
     5         10        15        20        25        30        35        40        45        50        55        60        65
     |         |         |         |         |         |         |         |         |         |         |         |         |
 1   AGACCTTAATTCGAAAGCGTATTCAACTTACCATATCTCGCGCCGAGGGAAGGACCATCGGCGCCAAC
41   AGGCCTTAATTCGAAAGCGTATTCGACATACCATATTTGCGCCGAGGGAAGATCCTTCGGCACAGAC 70        75        80        85        90        95       100       105       110       115       120       125       130       135
     |         |         |         |         |         |         |         |         |         |         |         |         |         |
     TACAGAGCCGTGGTTAGCGGACTCC-CAGTGCCGGCTCGGGAATAAGGTGTCACGAATTACCGGCAT    SEQ ID NO:19
     TACAGAGTCGAGGTGAGCGGCGCACACTGTGTCGGCTCGGGAATAAGGCTTGCACGAATTACCGGCAT  SEQ ID NO:20
```

CLASS VI

```
     5         10        15        20        25        30        35        40        45        50        55        60        65
     |         |         |         |         |         |         |         |         |         |         |         |         |
13   AGATGTGGTTGCATAGTAGGCAGCCGGGCACTTACGCCGGGCACTTACGCCGGGCACTTACGCCGGGCACTTACGCCGGATCGAGGACGAGACCG-AGCACCACGA
49   AGATGTGGGCGGCATAGTAGGCAGCCGGGCACTAACGCCAAATCGAAGACGAGACTGCGGCTCCACGA 70        75        80        85        90        95       100       105       110       115       120       125       130       135
     |         |         |         |         |         |         |         |         |         |         |         |         |         |
     TGGCGCCGCGATACCTCATTTGGGATTAGTGCCGGCTAGGAAAGTGAGTTCCTTATGACCTGCCTCCAC  SEQ ID NO:21
     TGCGCCGCGATGCCACTTTTGAGATTAGTGGGCTGGGAAAGTGAATTCCTTATGGCCTGTCTCCAC    SEQ ID NO:22
```

CLASS VII

```
     5         10        15        20        25        30        35        40        45        50        55        60        65
     |         |         |         |         |         |         |         |         |         |         |         |         |
47   AGATCGATTGGAGACGCCCTGGCGTACTTTAGGTAGAAAACTCCGACGGAAAAACTGCGGCACCGTG
62   CGTTAGATTGGAAGCGCCCCGACTTACTTTAGGTTGAAAACTCCGACGGAAAAA-CTACAGCACCGTG 70        75        80        85        90        95       100       105       110       115       120       125       130       135
     |         |         |         |         |         |         |         |         |         |         |         |         |         |
     GGAGTAGAGGATAGATAACAGG-CATTAGTGCCGGCCTCGCAAAGCTACCATGAGATTGGAGCGATCAGG  SEQ ID NO:23
     GGAGTAGAGGATAGGATATCAGGCATTAGTGCCGGCCTCGTAAAGCTACCAGGATATTGGGACGATCAGG SEQ ID NO:24
```

Fig. 5-3

Full-Length Cis-acting Ribozyme

Trans-acting Ribozyme random N72 pool
SEQ ID NO: 32  GGAACACTAT CCGACTGGCA CCNNNNNNNN NNNNNNNNNN NNNNNNNNNN NNNNNNNNNN
              NNNNNNNNNN NNNNCCTTGG TCATTAGGAT CG biotin aptamer doped pool
SEQ ID NO: 33  GGAGGCACCA CGGTCGGATC CNNNNNNNNN NNNggaacac tatccgactg gcaccgacca taggctcggg ttgccagagg
              ttccacactt tcatcgaaaa gcctatgcta tggactNNNN NNNNNNNNCC TTGGTCATTA GGATCG biotin ligator doped pool
SEQ ID NO: 34  GGAGGCACCA CGGTCGGATC Cggtttatta tcatgagccc gactcgacgg gcactgtaca taagcttcgg atgccatagt
              ttagacacta tggacgtaaa gcccatgcta ttgactgcat gagcgccgCC TTGGTCATTA GGATCG

Fig. 8D biotin aptamer clones

SEQ ID NO:35  NNNNNNNNNNNNNGGAACACTATCCGACTGGCACCGACCATAGGCTCGGGTTGCCAGAG
              GTTCCACACTTTCATCGAAAAGCCTATGCTAGGCAATGACATGGACTNNNNNNNNNNNN

SEQ ID NO:36  TTGCGGTGGGA----C----ATG----C--------------------AGG-T--C-A-----TAGGGGTTCACT
              --------G--------------------------------------------------------

SEQ ID NO:37  ATTTCGCGATGG----G-------AG-A--------------------------------A---
              ------------------------------------------------------------------

SEQ ID NO:38  TCTTCGGAGGCC--TT----G-CA-AC----------------------CC--C---------TGT--
              ---G-C--TG----------------------------------------------TTATCCACAAGT

SEQ ID NO:39  CAGTTATTCTGC--T--------------T----A------------------------CT---
              T-G---------------A----------------AC-T-----G-------------CCGGCATG--

SEQ ID NO:40  CAAAGGTCCTAC-------T---C--TA----A---------------CT---A---
              ---G-------T---G---------------TC----G----A-G-ATCACGTCTACT

SEQ ID NO:41  --CGCATCGTGCT---G---------------TCG----------------C---A---
              T--GT-T---A--T-T--------------------------------CCT-G------A---T-ACGCCCGCTGAG

SEQ ID NO:42  ACGTCCGCCAAC--TGG--------T--G--------C---------------G-C-C-
              --------T--T-------T----------------------G-----A---TTGAGGTAAAGT

SEQ ID NO:43  CCCTGTTAAAGA---------------T------CT-------------CGTT----
              ---G-------A-G---T--C-----T----------------GGT--C---

SEQ ID NO:44  CAAGAACCGGCC--A---A-------A-----T-------------C-----C
              A--A-----T---T-T--------------A--TC-GC-----CGT----CGCTAGCGGCATC

SEQ ID NO:45  TGGACTTTTCAC----------TG----T----------------C--T---------
              --G-----AC----T----------------------------------C-----CATCACAAAGGTT

Fig. 11 -1

```
SEQ ID NO:46  CTTCATTAAAGG----A---A-------------G-------------------T--TT----A
              -GCA-T-TG---G-G-----C--------------G-A-C------C-----ATTTGCCCAGAT

SEQ ID NO:47  TGATGAGAGCTAC-------CA----------------------------------T-------
              A----TTAC------T--T-----------------T--CT---------C-----T-TGAGAACA-----

SEQ ID NO:48  GACACAAAGCAG--C-----A---------------T-------------------T---C---
              C-------------------------------------T----CT----G-----GGACTCGATGTGT

SEQ ID NO:49  CCGAGCGGGTCGG---CG----T-------------------------------T-CT------
              C------A--C--T-G--------------------G---------------------------

SEQ ID NO:50  AGTGTCATATTA--G-----TA-C-------T---------------------T--G--CGC--
              --G-------G--A------C---------------G----T-C--A---C----ACAAACCCGATT

SEQ ID NO:51  CCCTAGTGGATA--------A--C------------------------------T--GA----C-
              T-------------------------------T-C--T----------------CACGCATTGCAT

SEQ ID NO:52  GTGCCGACTTAC--TT-----T---AA---------------------------T-----TA-C
              ---T--A-------------------------G-----C-GTTA--GT--TCGCAC--CGAT

SEQ ID NO:53  CTGCACAGGTAG--------G----T----------T-----C-----------TCA--G--TT
              -CG---C--A-----A----------------A--------T-----C-------GGTTCGTATCAT

SEQ ID NO:54  GACGGAACCGTTTT------G---------C-----------AA-T-T--C---A----ACTCGACCAGCA
              C-----ACA-------------------------------T---------

SEQ ID NO:55  GGGTCGTGGCGC--------A-----C--A-------------CC--------T----T--TT-
              -C-------C-------------------------------C----T----C----TTGGACGTCATT

SEQ ID NO:56  GCTCTGTTCGGTTC----A----AC-----------A-----------------T-------
              --G-----G--CAC------------------A--C-C--------T--CTCACGCTAGGCA
```

Fig. 11 -2

```
SEQ ID NO:57   ACACTATGTACT----A---G---ACA-------T-------T------TT-
               --G-----G---G---------GG---C-------C--T---GCCCAGTAACGT

SEQ ID NO:58   TGCTACTGTTAT-T---------CG-----------------T--T-----C
               ----GT-----G--T---C-------AA-TT----------C--G-CTAGGCGCGA

SEQ ID NO:59   TCTATGGCCGTGCA-------AC-A---T------C---------C-
               T---G--AGG-----------------G-TCT--------------CGGAAG-CCCAAT

SEQ ID NO:60   CTAAATTTGGTT-A---------G-A--------------T-----
               --G-TT---G---C--------TG-T--G---------T-----GAGGGATGCGGT

SEQ ID NO:61   GC-GAGGGCTCC---T-------G-A------TC---------A-----C
               C---A--TAC---T---------CG-T---G-C-----A--GCTCAATCAGTGT

SEQ ID NO:62   TGTCCGAACGAC-T-TGC-----------T---C-------A---TTC
               ---A---------------------GTT----G-CC------TCAGTAGATGGT

SEQ ID NO:63   CGGAATTACACT---T-------C---------------------T--
               C---A-----C-----------------C---TA--------------
```

Fig. 11 -3

```
                          biotin ligator clones         alkylation site
                                    ↓                        ↓
SEQ ID NO:64  GGTTTTATTATCATGAGCCCGACTCGACGGGCACTGTACATAAGCTTCGGATGCCATAG
                       H3                                H4
              TTTAGACACTATGGACGTAAAGCCCATGCTAGGCAAAGACATTGACTGCATGAGCGCCG
                                    H2

SEQ ID NO:65  -----C---GT-TTAAT-CCTA---CG-TCACA-T-GA-----C-GGG-A---TA---GAA
              -G---A-------A-----------A------G-A--T--T-----C-------GT---G---

SEQ ID NO:66  --GG-T---TGTCGCG-A---CT-G-----TT----------------------G-----
              AG---A----GC--------------T----T-G--T-TTA-ACCAA---AA---T---C---

SEQ ID NO:67  A-C---C--C------GTC-GT-CCACTCCACC-ACA-T---G----------T-----
              -AA--A---------------------G--ACG---C-C------T-----T---A-TT---

SEQ ID NO:68  -T-----GT---A-T--------AA--G-C------------C-C--------A-----
              -C-----G---T-GT--------------AT---A---G---C---T----T--------

SEQ ID NO:69  -T-----GC--TG-------CG---C----T-----C-GA-G-T-------------
              -CGC-----------------ATTG-T-G--T---C-----G-AG------CA-T----

SEQ ID NO:70  ----G-AATAAGC--TTAGGCCTA-TTGAC--T-A---GGC--T-AC------G-----
              ---T--------------------------GT---T-------T----------C----

SEQ ID NO:71  -AAA-T--G-GTGC--A-ACTACTCT-CT---C--TT-A------------------
              G---A-A-----------------G----A-C--T---C----G-T-------T----

SEQ ID NO:72  --G--T--T-A-GA-TGAGCT--ACT----G-GA----A-G-GA------------
              -AA--A--T-------------------TT--G---------A-T-A--C---T----

SEQ ID NO:73  ------C---GT-TTAAT-CCTA---CG---T---AT-TG-AT-C-GGG-A---TA--G--
              -G---A-------A-----------A------G-A--T--T-----C-------GT---G---
```

Fig. 11-4

| SEQ ID NO:74 | -----G-AA-A-------------A-T----------A-ACT-C--CGT-TCTAA--------------- |
| SEQ ID NO:75 | ---A---G-----ACCTT--G---TGGATCCTA--C--------GC---TCA--C-------G------ |
| SEQ ID NO:76 | --A-GC-------TC--C--TG---TG--A--------GT--GAC---GC-------------------C |
| SEQ ID NO:77 | ---AAA---C--ATAAGT-----T--G--CC---C--A---T---G-----A----------------- |
| SEQ ID NO:78 | --AAA--T---G--GTGC---A--ACTAC--CT--CT-----C---TA--A------------------ |
| SEQ ID NO:79 | ----G------G--T-----T---A-----C-----A----A-GA----T-----------C------- |
| SEQ ID NO:80 | --A-GC---------TC--C--TG----TG--A-----------G--TC--ACACC------------- |
| SEQ ID NO:81 | -AAA--T--G--GTGC---A--ACTACTCT--CT-----C--TT--A---------------------- |
| SEQ ID NO:82 | --A-------CAT---------G--GT--GA--A--TAT--AA-----T--T-----C-----A----- |
| SEQ ID NO:83 | -----AC-----ATGC---C--AACCTA---GG--CA--TG--C-----------T------------- |

Fig. 11 -5

```
SEQ ID NO:84   --AG-C---T-------------T--------TC-ACT--T---T--------C-------
               C-C--A--A--------------------------------A---TCTC--AG---------

SEQ ID NO:85   -A-------CAT-------G-GT-GA--A-TAT-AA----T-T-------C-----A--
               ---T--A---T-----------------------T----T---T---GATT----A---A-----T--

SEQ ID NO:86   -C-------C---TCTT-----TGA---C--------GGA----GAGG--A-G-------T
               ---A--G-----------------------------A---A------------TTG-C--AT----T------
```

Fig. 11 - 6

SEQ ID NO: 90

SEQ ID NO: 91

SELF-MODIFYING RNA MOLECULES AND METHODS OF MAKING

This invention was made with Government support under Contract #R01-GM45315-02 awarded by the National Institutes of Health. The Government has certain rights in this invention.

BACKGROUND OF THE INVENTION

This invention relates to novel ribozyme molecules and methods for their identification and isolation.

Both the genetic and enzymatic components of the earliest cells are thought to have been RNA molecules, because RNA is the only known macromolecule that can both encode information in a heritable form, and act as a biocatalyst (Joyce, *Nature* 338:217, 1989). It has been proposed that modern metabolism evolved prior to the evolution of encoded protein synthesis, and that early ribozyme-catalyzed metabolic transformations form the basis of our present protein-catalyzed metabolism (Bennet et al., *Proc. Natl. Acad. Sci. USA* 86:7054, 1989). This proposal requires that ribozymes should be able to catalyze a broad range of chemical transformations. However, to date, known natural ribozymes, including the group I and group II introns, RNAse P, and the hammerhead and hairpin RNAs, have been shown to catalyze only a restricted range of reactions involving the RNA sugar-phosphate backbone (Wilson and Szostak, *Curr. Opin. Struct. Biol.* 2:749, 1992).

SUMMARY OF THE INVENTION

The invention concerns a method for creating, identifying, and isolating catalytic RNA molecules capable of binding a ligand and catalyzing a reaction modifying the catalytic RNA (or other substrate). The method entails sequential selections for ligand binding RNA molecules and catalytic RNA molecules.

The ribozymes isolated by the method of the invention are capable of catalyzing reactions normally catalyzed by enzymes. Previously, the art disclosed ribozymes capable of catalyzing reactions involving the RNA sugar-phosphate backbone, e.g., phosphodiester transfer reactions and hydrolysis of nucleic acids. The methods of the invention can be used to create ribozymes capable of carrying out reactions on the RNA sugar-phosphate backbone. In addition, however, ribozymes created by the method of the invention can catalyze reactions other than hydrolysis and transesterification, thereby increasing the range of systems for which the catalytic ribozymes and the catalytic ribozyme selection systems of the invention are useful.

The methods of the invention entail sequential in vitro selections using pools of RNA molecules which include one or more regions of random sequence. Because catalysis of a complex reaction demands both the ability to bind a non-RNA ligand and the preferential stabilization of the transition state configuration of the reactants, the number of functional ribozymes in a pool of RNA having one or more regions of random sequence may be vanishingly small. The methods of the invention overcome this difficulty through the use of sequential selections. The method of the invention entails at least two selections steps: a binding selection step for identifying in a pool of random RNA molecules those RNA molecules which are capable of binding the selected ligand and a catalysis selection step for identifying in a pool of substrate binding RNA molecules (or sequence variants of such RNA molecules) those which are capable of catalyzing a reaction which modifies the catalytic RNA (or other substrate). After each selection step, an amplification step is performed. In this amplification step, the selected molecules are amplified using PCR. Of course, as explained more fully below, the binding selection step and the catalysis selection step may include one, two, or more rounds of selection and amplification. After each round, the pool of molecules is enriched for those having the desired binding or catalysis activity. Thus, the methods of the invention effectively entail three steps: 1) selection of RNA molecules capable of binding a chosen ligand from a pool of RNA molecules having a region of random sequence; 2) generation of a pool of RNA molecules which have a ligand binding sequence which is based on the identified ligand binding sequence of ligand-binding RNA molecules selected in step 1 as well as a region of random sequence; and 3) selection of RNA molecules exhibiting catalytic activity which modifies the RNA molecule itself or a substrate attached to the catalytic RNA. To identify catalytic RNA molecules one must tag the active molecules so that they may be partitioned from the inactive ones. This tagging is most straightforward when the reaction catalyzed by the RNA molecule modifies the catalytic RNA molecule itself. This modification can involve the formation of a chemical bond, the breaking of a chemical bond, or both. Often the modification attaches one or more new atoms to the RNA. Other desirable modifications remove one or more atoms from the RNA. To be useful for tagging the modification must render the modified molecules distinguishable from non-modified molecules. Tagging can also be accomplished by modification of a substrate attached to the catalytic RNA molecule. If all of the molecules in the pool are attached to a substrate molecule, those RNA molecules which can catalyze a reaction modifying the attached sustrate can be partitioned from the RNA molecules which do not carry out the modification.

Of course, one may find that a pool of catalytic RNA molecules is capable of carrying out a number of different modifications.

The selected ligand can include small molecules such as drugs, metabolites, cofactors, toxins, and transition state analogs. Possible ligands also include proteins, polysaccharides, glycoproteins, hormones, receptors, lipids, and natural or synthetic polymers. Preferably, for therapeutic applications, binding of the ligand and catalysis takes place in aqueous solution under physiological or near physiological salt conditions, temperature, and pH.

It is important to note that the ligand used to identify ligand-binding RNA molecules may be, but does not have to be, the same ligand which is used in the catalyst selection step. One may wish, for example, to isolate ligand-binding RNA molecules using a first ligand (e.g., ATP) and then isolate catalytic RNA molecules with a second ligand (e.g., ATP-γ-S) which can bind to the same ligand binding region.

As mentioned above, the method of the invention entails at least two selection steps. In the first step, RNA molecules capable of binding the chosen ligand are selected from a pool of RNA molecules which include one or more regions of random sequence. In the second selection step, RNA molecules capable of catalyzing a reaction modifying the RNA (or other substrate) are chosen from a second pool of random RNA molecules whose sequence is based on the sequence of one or more ligand binding RNAs identified in the first selection step.

"Random RNAs" and "random sequence" are general terms used to describe molecules or sequences which have one or more regions of "fully random sequence" and/or one or more regions of "partially random sequence." Such molecules may also include one or more regions of "defined sequence." "Fully random sequence" is sequence in which there is a roughly equal probability of each of A, T, C, and G being present at each position in the sequence. Of course, the limitations of some of the methods used to create nucleic acid molecules make it rather difficult to create fully random sequences in which the probability of each nucleotide occurring at each position is absolutely equal. Accordingly, sequences in which the probabilities are roughly equal are considered fully random sequences. In "partially random sequences" and "partially randomized sequences," rather than there being a 25% chance of each of A, T, C, and G being present at each position, there are unequal probabilities. For example, in a partially random sequence, there may be a 70% chance of A being present at a given position and a 10% chance of each of T, C, and G being present. Further, the probabilities can be the same or different at each position within the partially randomized region. Thus, a partially random sequence may include one or more positions at which the sequence is fully random and one or more positions at which the sequence is defined. Such partially random sequences are particularly useful when one wishes to make variants of a known sequence. For example, if one knows that a particular 20 base sequence binds the selected ligand and that positions 2, 3, 4, 12, 13, and 15–20 are critical for binding, one could prepare a partially random version of the 20 base sequence in which the bases at positions 2, 3, 4, 12, 13, and 15–20 are the same as in the known ligand binding sequence and the other positions are fully randomized. Alternatively, one could prepare a partially random sequence in which positions 2, 3, 4, 12, 13, and 15–20 are partially randomized, but with a strong bias towards the bases found at each position in the original molecule, with all of the other positions being fully randomized. This type of partially random sequence is desirable in pools of molecules from which catalytic RNAs are being selected.

As discussed below, the sequence of any randomized region may be further randomized by mutagenesis during one or more amplification steps as part of a process referred to as in vitro evolution.

It is desirable to have one, preferably two, regions of "defined sequence". Defined sequence is sequence selected or known by the creator of the molecule. Such defined sequence regions are useful for isolating and amplifying the nucleic acid because they are recognized by defined complementary primers. The defined primers can be used to isolate or amplify sequences having the corresponding defined sequences. The defined sequence regions preferably flank the randomized regions. The defined region or regions can also be intermingled with the randomized regions. Both the random and specified regions can be of any desired length.

In the first step, nucleic acids capable of binding the ligand are identified. Beginning with a pool of nucleic acids which include one or more regions of random sequence, the method for isolating ligand-binding molecules includes contacting the pool of nucleic acid with the substrate under conditions which are favorable for binding, partitioning nucleic acids which have bound the substrate from those which have not, dissociating bound nucleic acids and substrate, amplifying the nucleic acids (e.g., using PCR) which were previously bound, and, if desired, repeating the steps of binding, partitioning, dissociating, and amplifying any desired number of times.

Several cycles of selection (binding, partitioning, dissociating, and amplifying) are desirable because after each round the pool is more enriched for substrate binding nucleic acids. One can perform additional cycles of selection until no substantial improvement in substrate binding is observed. Of course, one can also perform far fewer cycles of selection.

In many cases, sequencing of nucleic acids isolated after one or more rounds of partitioning and amplification will reveal the presence of a number of different nucleic acids. One or more of these nucleic acids can be used in the pool of nucleic acids from which catalytic nucleic acids are isolated in the second selection of the method of the invention. Alternatively, the pool for the second phase can be composed of one or more nucleic acids having sequences based on the sequences of the nucleic acids identified in the binding selection. For example, sequencing of the nucleic acids which bind the substrate may suggest one or more regions of consensus sequence, i.e., sequences which appear to be important for binding. The pool of molecules used for selection of catalytic molecules may then include nucleic acids whose sequence is based on this consensus sequence. One may also employ a partially randomized sequence based on the consensus sequence. This may permit the isolation of improved binding domains. It can also permit alterations of the binding domain which may be desirable for improved catalysis. Of course, as discussed above, the degree of randomization of the consensus sequence is generally quite low. The consensus sequence region, randomized or not, may be interspersed with and/or flanked by additional randomized regions. Thus, the sequences of the molecules in the pool of nucleic acids molecules used in the catalysis selection step can differ from that of the molecule (s) identified in the substrate selection step as molecules capable of binding the desired substrate.

Those skilled in the art can readily identify ligand-binding consensus sequences by sequencing a number of ligand-binding RNA molecules and comparing their sequences. In some cases such sequencing and comparison will reveal the presence of a number of different classes of ligand binding sequences (aptamers). In these circumstances it may be possible to identify a core sequence which is common to most or all classes. This core sequence or variants thereof can be used as the starting point for the catalysis selection. By "variant" of a ligand binding sequence is meant a sequence created by partially randomizing a ligand binding sequence.

The size of the randomized regions employed should be adequate to provide a substrate binding site in the case of the binding selection step. Thus, the randomized region used in the initial selection preferably includes between 15 and 60 nucleotides, more preferably between 20 and 40 nucleotides. The randomized region or regions used for the catalysis selection step should be of sufficient length to provide a reasonable probability of being able to include catalytic activity.

The probability that any given RNA sequence of 30, 50, 100, or even 400 bases includes a region capable of binding a chosen substrate is very low. Similarly, the probability that a given RNA sequence which includes a region capable of binding a chosen substrate also has a region capable of catalyzing a reaction involving the chosen substrate is very low. Because of this each, of the two selection steps preferably begins with a pool of molecules which is large enough and random enough to include molecules which can bind the chosen substrate in the case of the binding selection or catalyze a reaction involving the chosen substrate in the case of the catalysis selection. Accordingly, the molecules used in each initial pool include at least one fully random sequence region. Binding sites may occur at a frequency of $10^{-10}$ to $10^{-15}$ in random sequences. Thus, pool sizes are preferably greater than $10^{10}$.

It is generally not practical to prepare a population of molecules which includes all of the possible sequences of a particular random sequence. However, even where one has a population of no more than $10^{15}$ different molecules out of $10^{60}$ potential sequences, one can isolate molecules having a desired binding or catalytic activity.

The catalysis selection step involves identifying RNAs which catalyze a reaction involving the chosen ligand. The pool of molecules used at the outset of this selection step generally is composed of molecules having one or more defined or partially randomized sequences which are designed to bind to the chosen ligand ("ligand binding region") as well as a second random sequence region, preferably fully randomized which serves as the source of potentially catalytic sequences. The ligand binding region included in the molecules in this catalysis selection pool can have a sequence which is identical to an identified ligand binding sequence identified in the binding selection phase. Alternatively the sequence of this region can be based on the consensus sequence of a number of substrate binding regions identified in the first step. The region may also be a partially randomized sequenced based on either a particular substrate binding sequence or substrate binding consensus sequence. Of course, the molecules also preferably include one or more defined sequence regions which can bind isolation or amplification primers.

In order to identify molecules having catalytic activity there must be a means for partitioning those RNA molecules which have catalyzed a reaction modifying the RNA molecule (or a substrate attached to the RNA) from those which have not. The selection can be accomplished using affinity columns which will bind modified, but not unmodified molecules. Alternatively, one can employ an antibody which recognizes the modified, but not unmodified molecules. It is also possible to chemically convert modified, but not unmodified ligand, to a compound which will bind selectively to an affinity column or other selective binding material (e.g., an antibody).

In many cases the catalytic RNA will itself be chemically altered (modified) by the reaction it catalyzes. This alteration can then form the basis for selecting catalytic molecules.

In many cases it may be possible to alter such catalytic RNA molecules so that instead of being self-modifying they modify a second molecule.

As will be apparent from the examples below there are a number of means for partitioning catalytic molecules from non-catalytic or less catalytic molecules.

It may be desirable to increase the stringency of a selection step in order to isolate more desirable molecules. The stringency of the binding selection step can be increased by decreasing ligand concentration. The stringency of the catalysis selection step can be increased by decreasing the ligand concentration or the reaction time.

One can covalently link a molecule to be modified to RNA so that catalytic RNA molecules can be isolated by isolating the modified molecule. For example, one might wish to find RNAs capable of oxidizing compound A. This might be accomplished by isolating RNA molecules capable of binding a redox co-factor (NAD, FAD, or NADP). A pool of random RNAs is then created which are capable of binding the cofactor. Compound A is then covalently attached to the RNA molecules in this pool and a selection is carried out which isolates molecules having the oxidized form of compound A. Methods for linking various compounds to RNA are well known to those skilled in the art and include the use of a thiophosphate group and the use of amines linked via a 5' phosphate.

Of course, in some cases a catalytic RNA which is capable of self-modification or modification of an attached substrate may also be able to perform the "trans" reaction. Such trans acting molecules modify an RNA other than themselves or modify the substrate even when it is not attached to the catalytic RNA.

In one aspect, therefore, the invention features a method for producing a catalytic RNA molecule capable of binding a first ligand and catalyzing a chemical reaction modifying the catalytic RNA molecule. The method includes the following steps:

a) providing a first population of RNA molecules each having a first region of random sequence;

b) contacting the first population of RNA molecules with the first ligand;

c) isolating a first ligand-binding subpopulation of the first population of RNA molecules by partitioning RNA molecules in this first population which specifically bind the first ligand from those which do not;

d) amplifying the first ligand-binding subpopulation in vitro;

e) identifying a first ligand binding sequence;

f) preparing a second population of RNA molecules each of the RNA molecules including the first ligand binding sequence and a second region of random sequence;

g) contacting the second population of RNA molecules with a second ligand capable of binding the first ligand binding sequence; and h) isolating a subpopulation of the catalytic RNA molecules from the second population of RNA molecules by partitioning RNA molecules which have been modified in step g) from those which have not been modified.

In various preferred embodiments of the method, the first ligand is ATP, the first ligand is biotin, the second ligand serves as a substrate for the chemical reaction, and the first and second ligands are the same.

In other preferred embodiments of the method, the catalytic RNA molecule can transfer a phosphate from a nucleotide triphosphate to the catalytic RNA molecule. In more preferred embodiments of the method, the transfer is to the 5'-hydroxyl of the catalytic RNA molecule and the transfer is to an internal 2'-hydroxyl of the catalytic RNA molecule.

In another preferred embodiment of the method, the catalytic RNA molecule can transfer a phosphate from a nucleotide triphosphate to a nucleic acid (preferably, a ribonucleic acid) other than the catalytic RNA molecule.

In another preferred embodiment of the method, the catalytic RNA molecules can catalyze N-alkylation, the catalytic RNA molecule can catalyze N-alkylation of the catalytic RNA molecule, and the catalytic RNA molecule can catalyze N-alkylation of a nucleic acid other than the catalytic RNA molecule.

In another aspect, the invention features a catalytic RNA molecule which can transfer a phosphate from a nucleotide triphosphate to the catalytic RNA molecule. In preferred embodiments, the transfer is to the 5'-hydroxyl of the catalytic RNA molecule and the transfer is to an internal 2'-hydroxyl of the catalytic RNA molecule.

In another aspect, the invention features a catalytic RNA molecule which can transfer a phosphate from a nucleotide triphosphate to a nucleic acid (preferably, a ribonucleic acid) other than the catalytic RNA molecule.

In another aspect, the invention features a catalytic RNA capable of catalyzing N-alkylation. In preferred embodiments, the catalytic RNA molecule can catalyze N-alkylation of the catalytic RNA molecule, and the catalytic RNA molecule can catalyze N-alkylation of a nucleic acid other than the catalytic RNA molecule.

In another aspect, the invention features a method for producing a catalytic RNA molecule capable of binding a first ligand and catalyzing a chemical reaction modifying a first substrate molecule bound to the catalytic RNA molecule. The method entails the following steps:

a) providing a first population of RNA molecules each having a first region of random sequence;

b) contacting the first population with the first ligand;

c) isolating a first ligand-binding subpopulation of the first population of RNA molecules by partitioning RNA molecules in the first population of RNA molecules which specifically bind the first ligand from those which do not;

d) amplifying the first ligand binding subpopulation in vitro;

e) identifying a first ligand binding sequence;

f) preparing a second population of RNA molecules each of the RNA molecules including the first ligand binding sequence and a second region of random sequence, each of the RNA molecules being bound to the first substrate molecule;

g) contacting the second population of RNA molecules with a second ligand capable of binding the first ligand-binding sequence; and h) isolating a subpopulation of the catalytic RNA molecules from the second population of RNA molecules by partitioning RNA molecules which are bound to a substrate molecule which has been modified in step g) from those RNA molecules which are bound to a substrate molecule which has not been modified in step g).

In a preferred embodiment of this method, the second ligand serves as a second substrate for the chemical reaction.

The invention also features ribozymes having polynucleotide kinase activity. Such ribozymes have 80%, preferably 85%, more preferably 95% homology to any of classes I–VII polynucleotide kinase ribozymes described in FIG. 5. More preferably such ribozymes have 90% (more preferably 95%) homology to the core catalytic region of any of these classes of ribozymes. The core catalytic region is the minimal sequence required for catalytic activity. This sequence can be determined using standard deletion analysis.

The invention also features ribozymes capable of carrying out an alkylation reaction. In a preferred embodiment the ribozyme has 90%, and preferably 95% homology to BL-E.

Other features and advantages of the invention will be apparent from the description of the preferred embodiments, and from the claims.

BRIEF DESCRIPTION OF THE DRAWINGS

FIG. 5 illustrates the sequences of molecules representing the seven major kinase classes (50 clones sequenced) (SEQ ID NO:6To SEQ ID NO:24). Arrows delimit the ATP aptamer conserved loop. The Ban I site used for pool construction (see FIG. 2) is underlined. Complementarity between the random region and the (constant) 5'-end of the RNA is shaded (Classes I and V). Both of these classes are 5'-kinases; these regions may serve to bind the 5'-end in the active site of the ribozymes. Sites of 2'-thiophosphorylation are shown as white letters in black boxes. Clone Kin. 47 is inactive, and contains a G to A mutation at the site of 2'-thiophosphorylation. The sequences of the constant primer binding regions (see FIG. 2) are not shown except for the first three bases following the 5' primer binding site (AGA). The length of the original pool (not including primer binding sites) was 138 nucleotides. Point deletions may have occurred during the chemical synthesis of the pool DNA, and larger deletions may be due to annealing of primers to sites in the random regions during reverse-transcription or PCR.

FIG. 8D shows coding sequences for RNA pools used for in vitro selection experiments (SEQ ID NO:32 to SEQ ID NO: 34). Upper case A, C, G, T: pure nucleotide. N: equimolar mix of A, C, G, T. Lower case a, c, g, t: 70% major nucleotide, 10% each of three minor nucleotides. Underline: constant primer sequences used for amplification.

FIG. 11 illustrates functional biotin binder and biotin ligator sequences (SEQ ID NO:35 to SEQ ID NO:86). The partially-randomized pool sequence is shown above each set of sequences. Deviations from the principle nucleotide at each position are explicitly written while conservation of the wide type base is indicated with a dash. Biotin aptamer and self-biotinylating RNA partially-randomized pools were re-selected for biotin-agarose binding and self-biotinylation respectively. Biotin aptamer sequences correspond to clones from the fourth round of re-selection. Self-biotinylating ribozyme clones were sequenced after eight rounds of re-selection, when the overall biotinylation activity of the pool was 100 times the activity of the initial BL8-6 ribozyme. Arrows are used to indicate the locations of proposed helices. Boxed nucleotides are highly conserved yet not involved in secondary structure.

FIG. 12A (SEQ ID NO:90) is a complete sequence of the BBS-5 biotin aptamer, shown as the proposed pseudoknot. FIG. 12B (SEQ ID NO: 91) is a sequence and proposed cloverleaf structure for the BL8-6 self-biotinylating ribozyme. The guanosine residue that serves as the alkylation site for the biotinylation reaction is circled.

DESCRIPTION OF THE PREFERRED EMBODIMENTS

EXAMPLE 1

Figure 1:
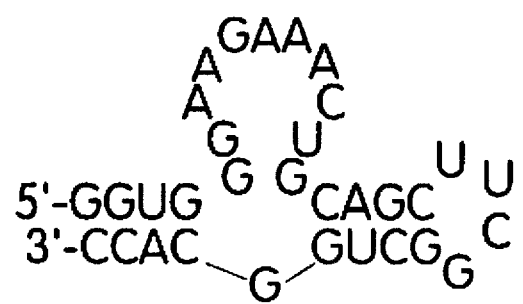
FIG. 1 is a schematic illustration of a minimal ATP aptamer (SEQ ID NO:4).

In one example of the invention, RNA molecules which bind ATP were first isolated from a pool of random RNA. RNA molecules capable of binding ATP were sequenced, and the information obtained was used to design a second pool of RNA molecules which included an ATP binding site or variant thereof. This pool was then subjected to selection and amplification to identify RNA molecules having polynucleotide kinase activity.

Selection of ATP-binding RNAs

The selection of ATP-binding RNAs was carried out in a manner designed to ensure selection of RNAs capable of binding ATP in solution as well as on an insoluble support. This was accomplished by selecting RNA molecules which bound an ATP-sepharose column and could be eluted using ATP.

A chemically synthesized pool of DNA molecules containing a central region of 120 random nucleotides 5 flanked by constant regions used as primer binding sites was PCR-amplified and transcribed in vitro by T7 RNA polymerase in the presence of [$\alpha$-$^{32}$P]GRP. RNA was ethanol-precipitated and unincorporated nucleotides removed by Sephadex-G50 chromatography. Following a brief incubation at 65° C. in binding buffer (300 mM NaCl, 20 Mm Tris, pH 7.6, 5 mM MgCl$_2$), the RNA was cooled to room temperature before being loaded onto a 1-ml ATP agarose affinity column. The affinity matrix contained ~1.6 mM ATP linked through its C8 position through a diaminohexyl linker to cyanogen bromide-activated agarose (Sigma, St. Louis, Mo.). After washing with 6 column-volumes of binding buffer, bound RNAs were eluted with 3 column-volumes of binding buffer containing 4 mM ATP, then concentrated by precipitation with ethanol. For the first three cycles, an agarose pre-column was used to prevent enrichment of the RNA pool with agarose-binding RNAs, and bound RNAs were eluted with 5 mM EDTA in water rather than affinity-eluted with ATP. After reverse transcription and PCR amplification, DNA templates were transcribed and the resulting RNA was used in the next round of selection. RNA from the eighth round of selection was converted to cDNA, amplified as double-stranded DNA by PCR, digested with EcoR1 and BamHI gel-purified and cloned into the phage M13 based vector pGem3Z (Promega, Madison, Wis.).

Thirty-nine clones from the eighth cycle RNA population were sequenced seventeen different sequences were found. Of these, the most abundant sequence (C8-ATP-3) occurred 14 times, and 12 sequences occurred just once. Comparison of the seventeen different sequences revealed an 11-nucleotide consensus sequence, of which seven positions are invariant among all clones but one (C8-ATP-15). Clones 2, 3, 8, 15, and 19 were individually tested for binding to ATP-agarose. All had a dissociation constant ($K_d$) of less than 50 µM, except for C8-ATP-15, for which the estimated $K_d$ was ~250 µM.

To determine the minimal sequence for ATP binding, deletions of C8-ATP-3 were analyzed. An active RNA molecule 54 nucleotides in length (ATP-54-1) was generated by a combination of 5' and 3' deletions. This RNA can be folded into a secondary structure in which the 11-base consensus is flanked by two base-paired stems. Deletion of the left-hand stem abolished ATP-binding activity; dimethylsulphate modification experiments also supported the proposed secondary structure. Comparing sequences of all the clones showed that they all had a potential to fold into this secondary structure. This analysis also highlighted the presence of an invariant unpaired G opposite the 11-base consensus. The orientation and distance of this G and its flanking sequences relative to the consensus sequence was variable from clone to clone. The stems flanking the conserved G and the consensus were variable in length and composition, and frequently contained G-U base pairs. The simplest explanation for the observation that all of the selected clones contained a single consensus sequence embedded in a common secondary structure is that these clones contain the shortest sequences capable of binding ATP with the necessary affinity, and that all other sequences with comparable or superior affinity are longer and hence less abundant in the initial random sequence pool.

On the basis of these findings, a smaller RNA of 40 nucleotides (ATP-40-1) was designed, in which the consensus sequence was flanked by stems of six base pairs, with the right-hand stem closed by a stable loop sequence for enhanced stability. This RNA bound ATP as well as the full-length 164-nucleotide RNA C8-ATP-3 and was used for later experiments. Variant 40-oligonucleotide RNAs were also synthesized to test the importance of the highly conserved unpaired G (residue G34 in ATP-40-1) for ATP binding. Deleting this residue or changing it to an A residue eliminated binding, confirming the results of the selection experiments.

To determine which functional groups on the ATP are recognized by the ATP-binding RNA, we examined the ability of a series of ATP analogues to elute bound ATP-40-A RNA from an ATP-agarose column. Methylation of positions 1, 2, 3, or 6 on the adenine base, or the 3' hydroxyl of the ribose sugar, abolish binding, as does removal of the 6-amino or 2'_hydroxyl. Positions 7 and 8 on the base can be modified without effect; this is not surprising considering that selection was for binding to ATP linked to an agarose matrix through its C8 position. Adenosine, AMP, and ATP are equally efficient at eluting the RNA, suggesting that the 5' position on the ribose moiety is not recognized by the RNA.

Isocratic elution (Arnold et al., *J. Chromatography* 31:1, 1986) from ATP-agarose and equilibrium gel filtration (Fersht, in Enzyme Structure and Mechanism p. 186–188, Freeman, New York, 1985) was used to measure the dissociation constant for the RNA-ATP complex on the column and in solution. The $K_d$ of ATP-40-1 was ~14 µM when measured by isocratic elution from an ATP-C8-agarose column, and 6–8 µM by equilibrium gel filtration. The $K_d$ for the ATP-agarose complex is an upper estimate, because the fraction of bound ATP that is accessible to the RNA is not known. The solution $K_d$ for adenosine was similar to that of ATP (5–8 µM), but the $K_d$ for dATP was not measurable (>1 mM). The $K_d$ of ATP-40-1 for its ligand dropped to 2 µM when the $Mg^{+2}$ concentration was raised from 5 to 20 mM. Changing the base pair U18-A33 to C-G, as found in most of the clones initially selected, further decreased the $K_d$ to 0.7 µM. At almost saturating concentrations of ATP (50 µM), the RNA bound ~0.7 equivalents of ATP. The RNA likely binds its ligands with a stoichiometry of unit.

Kethoxal modification (Moozod et al., *J. Mol. Biol.* 187:399, 1987) was used to assess the accessibility of guanosine residues to modification. G7 and G17 within the loop, and G6 (which forms the G-C base pair on the left side of the loop), all of which are strongly protected in the absence of ATP, become highly accessible to modification by this reagent in the presence of ATP. Other guanosine residues, including G8 in the large loop, the single unpaired G opposite the loop, and Gs in the stems, are highly protected in the presence or absence of ATP. These observations suggest that the motif is highly structured both in the presence and absence of ATP, but that binding induces a conformational change in the structure of the RNA.

A pool of random sequence RNAs, using the above-identified minimal ATP aptamer as a core structure was prepared and used to create polynucleotide kinase ribozymes. The ATP aptamer is based on that described by Sassanfar and Szostak (*Nature*, 364:550,1993).

Selection of Catalytic RNAs

Figure 2:
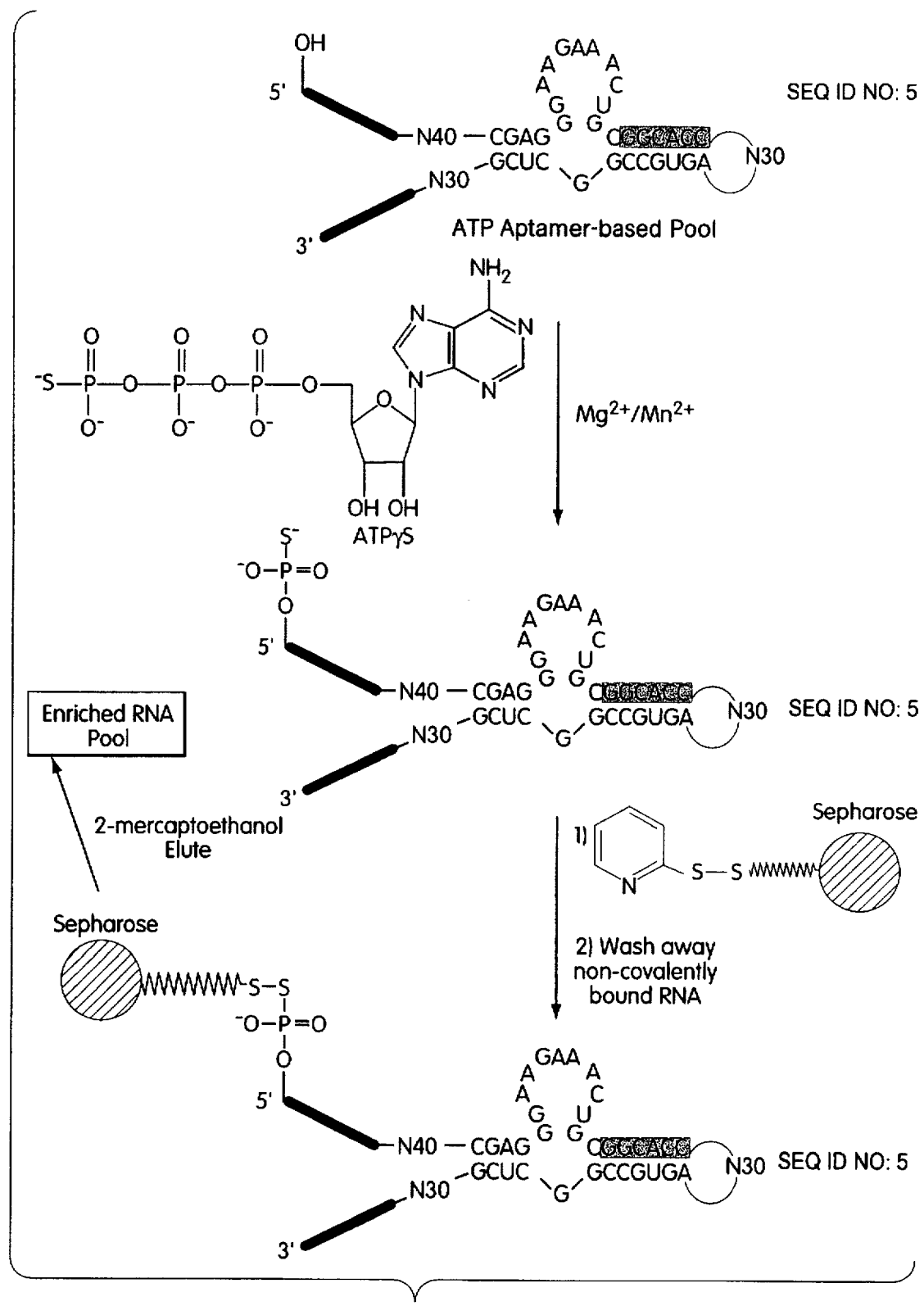
FIG. 2 is a schematic illustration of the random RNA pool built around the ATP aptamer structure and the selection scheme (SEQ ID NO:5). The pool contained three regions of random sequence (N) for a total of 100 randomized bases. The aptamer region was mutagenized to a level of 15%. The Ban I site used to ligate the two halves of the pool is shown in gray. Constant primer binding sites are shown as thick lines. Random pool RNA was allowed to react with ATP-γ-S and thiophosphorylated molecules were isolated by reaction with thiopyridine-activated thiopropyl sepharose. Non-specifically bound molecules were removed by washing under denaturing conditions. Active molecules were eluted with 2-mercaptoethanol. Constant regions: 5'-GGAACCUCUAGGUCAUUAAGA-3' (5'-end constant region) (SEQ ID NO:1); 5'-ACGUCAGAAGGAUCCAAG-3' (3'-end constant region) (SEQ ID NO:2).

A pool of RNA molecules for selection of catalytic RNAs was created based on a minimal ATP aptamer core sequence (FIG. 1). The ATP aptamer core was surrounded by three regions of random sequence, 40, 30, and 30 nucleotides in length as shown in FIG. 2. The ATP-binding domain itself was mutagenized such that each base had a 15% chance of being non-wild type, to allow for changes in the aptamer sequence that might be required for optimal activity. To increase the likelihood of finding active molecules, an effort was made to create a pool containing as many different molecules as possible. Because it is difficult to obtain an acceptable yield from the synthesis of a single oligonucleotide of this length (174 nucleotides), two smaller DNA templates were prepared and linked together to generate the full length DNA pool (FIG. 2) (Bartel and Szostak, *Science*, 261:1411, 1993). The presence of constant primer binding sites at the 5' and 3' ends of the molecules permitted amplification by PCR. Transcription of this DNA pool yielded between $5 \times 10^{15}$ and $2 \times 10^{16}$ different RNA molecules.

In order to select for catalytic activity, it is necessary to tag active molecules so that they can be separated from inactive ones. To accomplish this, the random sequence RNA pool was incubated with ATP-γ-S and the transfer of the thiophosphate from ATP-γ-S to the RNA was selected for chromatography on a thiopyridine-activated thiopropyl sepharose column, which forms disulfide bonds with RNAs containing thiophosphate groups. Molecules without thiophosphates were washed away under denaturing conditions. RNAs linked via a disulfide to the column matrix were eluted with an excess of 2-mercaptoethanol. This overall scheme is illustrated in FIG. 2. Briefly, the pool was incubated with ATP-γ-S under conditions designed to promote the formation of RNA tertiary structure (400 mM KCl, 50 mM $MgCl_2$, 5 mM $MnCl_2$, 25mM HEPES, pH 7.4). $Mn^{2+}$ was included because of its ability to coordinate phosphorothioates. Streptavidin agarose immobilization of pool RNA was used during the first seven cycles to prevent pool aggregation. After cycle 7, the ATP-γ-S reaction step was performed in solution (1 μM RNA). For the first cycle, 2.4 mg (40 nmoles; 5 pool equivalents) of random pool RNA was used, in the second cycle 150 μg (2.4 nmoles) RNA was used, and in succeeding cycles 60 μg (1 nmole) was used. The selection step was performed by incubating the RNA with thiopyridine-activated thiopropyl sepharose-6B (Pharmacia, Piscataway, N.J.) in 1 mM EDTA, 25 mM HEPES, pH 7.4 for 30 minutes at room temperature. The resin was then washed with 20 column volumes each of wash buffer (1M NaCl, 5 mM EDTA, 25 mM HEPES, pH 7.4), water, and finally 3M urea, 5 mM EDTA to eliminate molecules without thiophosphates. RNAs linked to the resin via a disulfide were eluted with 0.1M 2-mercaptoethanol in 0.5× wash buffer. Reverse-transcription, PCR and transcription yielded a new RNA pool enriched in active molecules. This process comprised one cycle of selection.

Prior to each cycle of the selection, the pool RNA generated by transcription was exhaustively dephosphorylated with calf intestinal alkaline phosphatase to remove the 5'-triphosphate, and any other phosphates that might have been transferred to the RNA by autophosphorylation during transcription.

The selection protocol demanded only that an RNA molecule contain a thiophosphate in order for it to be isolated. Reactions that could have been selected for include: transfer of the γ-thiophosphate from ATP-γ-S to the 5'-hydroxyl of the RNA (analogous to the reaction catalyzed by T4 polynucleotide kinase), to the 3'-end of the RNA, to an internal 2'-hydroxyl, or even to a group on one of the bases. Transfer of diphosphate (or perhaps the entire triphosphate) instead of a single thiophosphate is also possible for all of these reactions. A splicing reaction, in which ATP-γ-S displaces one of the first few nucleotides of the RNA in a manner analogous to the reaction catalyzed by the Group I introns, could also occur. However, cleavage of more than the first few bases of the RNA would result in a molecule lacking a 5'-primer binding site, and such a molecule would not be amplified during the PCR step of the selection. Similarly, any reaction that blocked reverse transcription would not be selected for.

Figure 3:
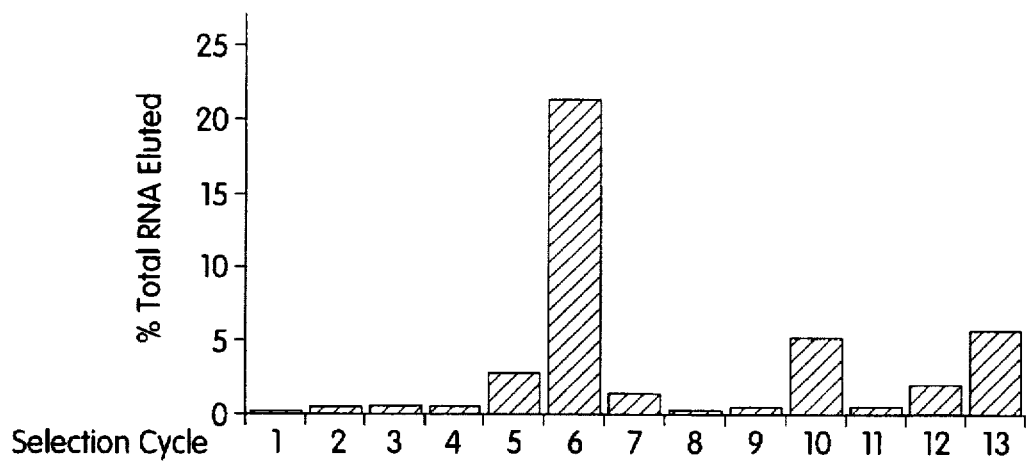
FIG. 3 is a graph showing the percent RNA eluted by 2-mercaptoethanol from the thiopyridine-activated thiopropyl Sepharose at each cycle of selection. Background sticking and elution from the resin is approximately 0.5%. The concentration of ATP-γ-S used in each selection and the incubation time for each selection is shown below the graph. Also indicated is whether the selection entailed mutagenic PCR.

The progress of the selection process was monitored by measuring the fraction of the pool RNA that bound to the thiopropyl Sepharose and was eluted with 2-mercaptoethanol (FIG. 3). Initially, ~0.5% of the RNA bound nonspecifically to the matrix and was eluted by 2-mercaptoethanol. After five cycles of selection, greater than 20% of the pool RNA reacted with thiopropyl Sepharose. Since there were at least 10,000 different molecules left in the pool at this stage, the stringency of the selection in the succeeding cycles was increased by lowering the ATP-γ-S concentration and the incubation time, in order to try to isolate the most active catalysts.

Optimization of Catalytic RNAs

Figure 4:
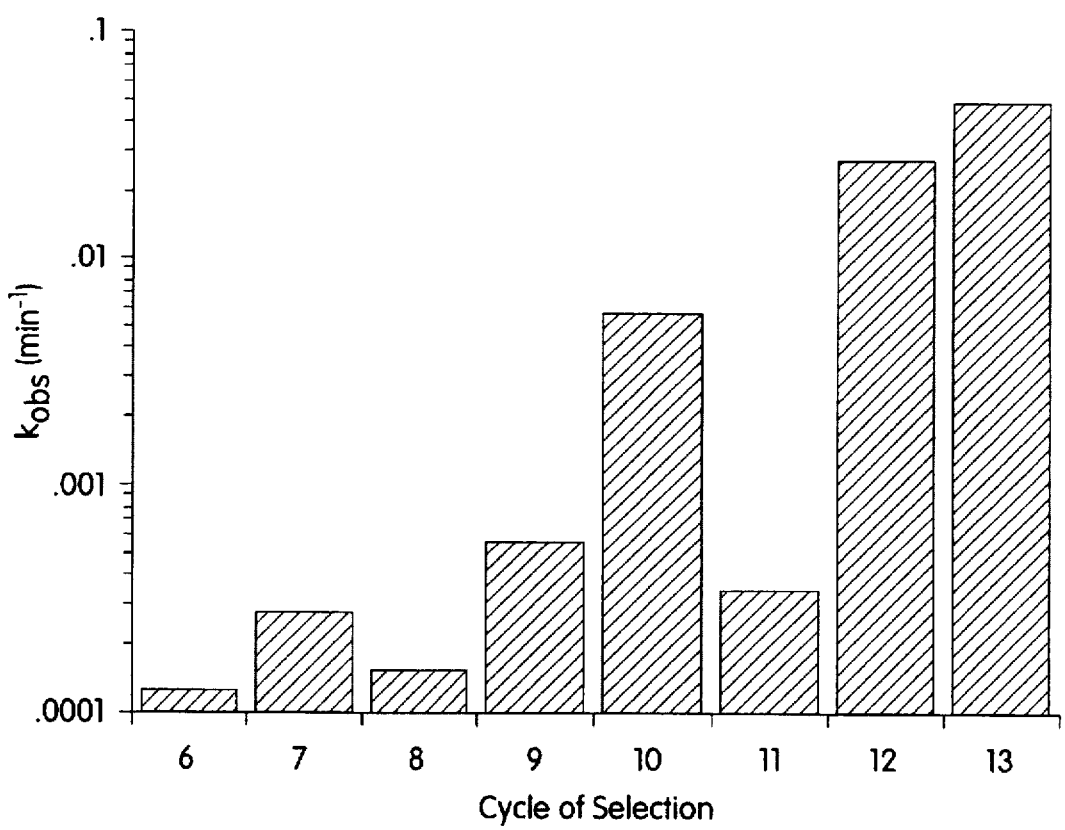
FIG. 4 is a graph showing the $k_{obs}$ of pool RNA for selection cycles 6–10, 12 and 13. Reactions were performed with 100 μM ATP-γ-S, and a time point was chosen such that >20% of the pool had reacted. At cycle 6, the activity of the pool could be readily detected. The following seven cycles increased the activity by nearly three orders of magnitude. The drop in $k_{obs}$ in cycle 8 is presumably due to the effects of mutagenic PCR, coupled with the fact that the pool was no longer immobilized on streptavidin in this cycle. Cycle 11 activity declined for unknown reasons.

Because the random pool initially prepared sampled sequence space very sparsely (there are between $4^{100}$ and $10^{60}$ possible 100-mers, but only approximately $10^{16}$ different molecules in the pool), active molecules are likely to be sub-optimal catalysts. Accordingly, three cycles of mutagenic PCR (before selection cycles 7, 8, and 9) were performed to allow the evolution of improvements in the active molecules. Mutagenic PCR was performed as described by Bartel and Szostak (*Science*, 61:1411, 1993) and by Cadwell and Joyce (*PCR Methods Appl.*, 28, 1992). Briefly, thirty total cycles of PCR were done at each round to yield ~2% mutagenesis. Reactions of pool RNAs were performed either with trace ATP-γ-$^{35}$S, or with 100 μM ATP-γ-S plus additional trace ATP-γ-$^{35}$S. Dithiothreitol (DTT, 10 mM) was included in the reactions. Reactions were quenched by the addition of one volume of 150 mM EDTA, 20 mM DTT in 95% formamide. Reactions were analyzed by electrophoresis on 10% polyacrylamide/8M urea gels. Quantitation was performed using a PhosphorImager (Molecular Dynamics). A known amount of ATP-γ-$^{35}$S was spotted on the gels as a standard. The combined effect of increasing the stringency and performing mutagenic PCR was to increase the activity of the pool by nearly three orders of magnitude from cycle 6 to cycle 13 (FIG. 4).

Catalytic RNAs Identified

After 13 cycles of selection, RNA molecules from the pool were cloned using the pT7 Blue T-Vector kit by Novagen, and 50 clones were sequenced. The clones sequenced (FIG. 5) fall into seven classes of two or more closely related molecules (19 clones) and 31 unique sequences. Each class of sequences represents molecules with a common ancestor that acquired mutations during the course of the mutagenic PCR done in cycles 7–9 of the selection.

Figure 6:
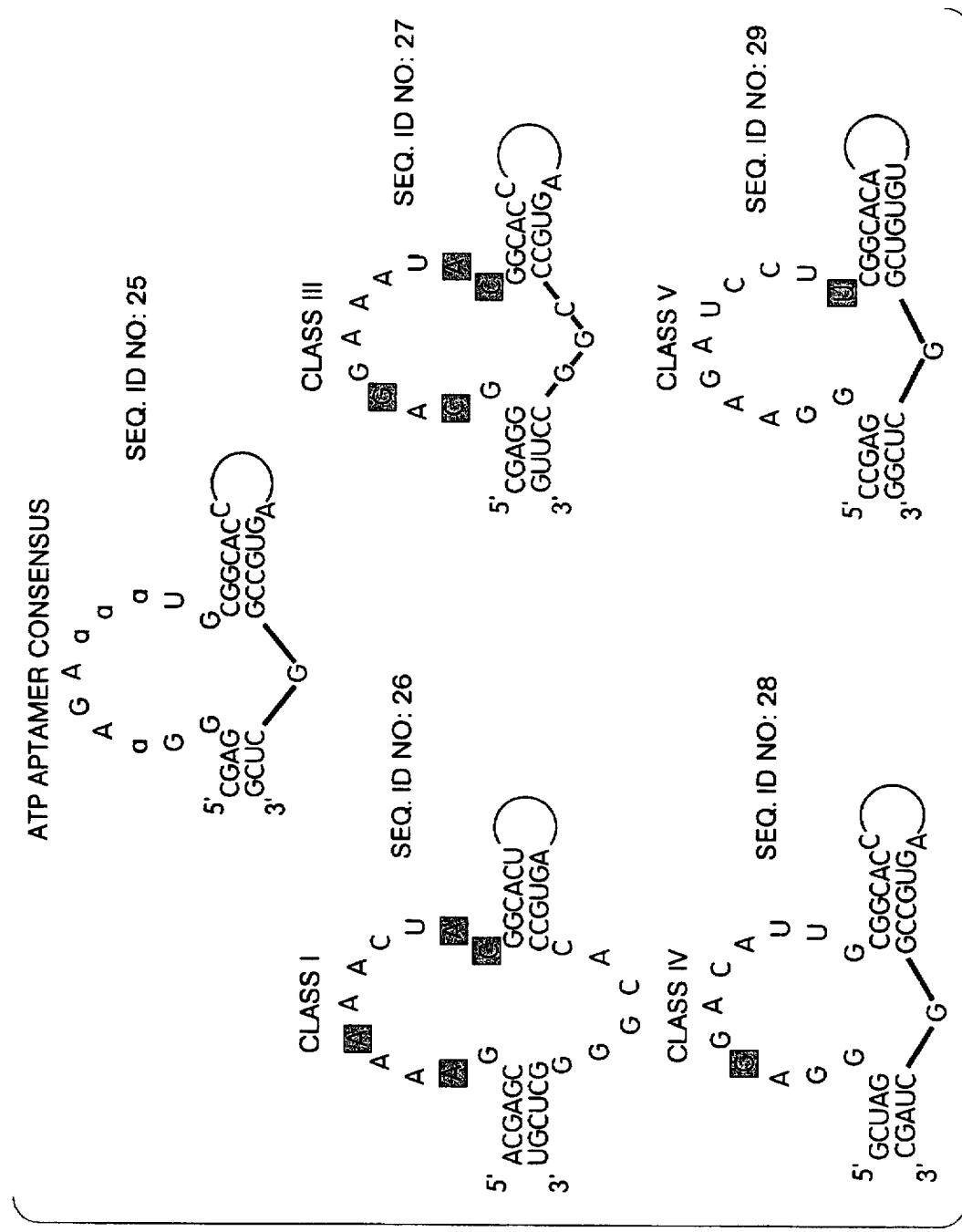
FIG. 6 is a set of schematic illustrations of proposed structures of the ATP aptamer consensus and several classes of ATP aptamer (SEQ ID NO:25 to SEQ ID NO:29). In the illustration of the consensus aptamer conserved bases in the loop are shown in capital letters. Positions that tend to be A, but which can vary, are shown as "a"s. The bulged G is also conserved, but the stem regions (aside from being base paired) and the right hand loop are not. For the schematic illustrations of possible secondary structures of the ATP aptamer domains of four of the major classes of ribozymes, the sequence of the most active clone is shown in each case. Positions in the loop regions that differ from the consensus sequence for the ATP aptamer are highlighted in gray. One of the stem regions from each of Classes II, VI and VII is missing, and so these structures are not shown.

Comparison of the sequences in the seven major classes of molecules reveals significant conservation of the sequence of the original ATP binding site in some of the active RNAs. FIG. 6 shows the putative structures for the ATP aptamer regions from Classes I, III, IV and V, the classes for which an aptamer-like structure can be drawn. It appears that Classes I and III have changed significantly from the original ATP binding domain, whereas Classes IV and V are only slightly different from the ATP aptamer consensus sequence described by Sassanfar and Szostak (*Nature*, 364:550, 1993). Either the right or left hand stems of the Class II, VI and VII aptamer regions appear to be missing, and it seems likely that these molecules have found novel modes of binding their substrates. Using run-off transcription of synthetic DNA oligonucleotides (Milligan and Uhlenbeck, *Methods Enzymol.* 180:51, 1989) the RNAs corresponding to the Class I, III, IV, and V aptamer regions were produced. The Class IV aptamer RNA binds weakly to C-8 linked ATP agarose (Sassanfar and Szostak, supra), consistent with a molecule having a $K_d$ for ATP in the range of 0.05–0.5 mM. The Class I, III, and IV aptamers, on the other hand, do not detectably interact with ATP agarose, consistent with $K_d$s>0.5 mM for ATP (if they bind ATP at all). Presumably, the corresponding classes of kinases have developed novel modes of binding ATP-γ-S.

Characterization of the Catalyzed Reactions

Pool 13 RNA and the members of each of the major classes of kinases were tested to determine what reactions they catalyze. Nuclease P1 analysis was performed as follows. RNA (1 μM) was allowed to react with ~1μM ATP-γ-$^{35}$S in reaction buffer for 4-18 hours. The RNA was the separated from nucleotides by G-50 spin column gel filtration (Boehringer-Mannheim, Indianapolis, Ind.). The RNA was digested with nuclease P1 as described in Westaway et al. (*J. Biol. Chem.* 268:2435, 1993) and Konarska et al. (*Nature* 293:112, 1981). An aliquot was then spotted directly onto a PEI cellulose TLC plate (Baker, Phillipsburg, N.J.) and developed in 1M LiCl, 10 mM DTT (as described in Westaway, supra). The products were localized by UV shadowing (for unlabelled GMPαS) or autoradiography. Thiophosphate containing nucleotides run slower in this system than do the corresponding phospho-nucleotides, presumably because there is weaker interaction between Li$^+$ and the thiophosphate than there is with the phosphate.

PEI cellulose thin layer chromatography (TLC) of nuclease P1 digests of auto-thiophosphorylated RNA shows two major radiolabeled products, demonstrating that at least two different reactions are catalyzed by the pool 13 RNAs. If a particular RNA molecule transfers the γ-thiophosphate from ATP-γ-S to its own 5'-hydroxyl, the nuclease P1 digestion should yield labeled GMPαS, since all of the RNAs begin with guanosine. All members of Classes I, II, III, V, and VI yield GMPαS as the sole nuclease P1 digestion product, indicating that they are 5'-kinases. Classes IV and VII, on the other hand, yield a nuclease P1 digestion product that does not migrate from the origin in the TLC system used. Both RNase T2, which hydrolyzes RNA to nucleotide 3'-monophosphates, and nuclease P1 digestion of reacted Class IV and Class VII RNAs, give products that run as molecules with charges of −5 to −6 on DEAE cellulose TLC plates, using a solvent system that separates based upon the charge of the RNA fragment (Dondey and Gross, *Anal. Biochem.* 98:346, 1979; Konarska et al., *Nature* 293:112, 1981). These data are consistent with Class IV and VII RNAs being internal 2'-kinases, since neither nuclease P1 nor RNase T2 can cleave at 2'-phosphorylated sites (Westaway et al., *J. Biol. Chem.* 268:2435, 1993). The products of these digestions, then, should be $^{35}$S-labeled dinucleotides with 5'-phosphates or 3'-phosphates (for nuclease P1 and RNase T2 digestions, respectively) and 2'-mono- or di-phosphates.

Experiments in which the RNAs were allowed to react with unlabeled ATP-γ-S and were then purified and reacted with ATP-γ-$^{32}$P and T4 polynucleotide kinase support the proposal that Classes I, II, III, V, and VI are 5'-kinases, and that Classes IV and VII phosphorylate some internal site. As expected, reaction products from Classes I, II, III, V, and VI cannot be labeled by T4 polynucleotide kinase, consistent with their being 5'-kinases. Class IV and VII RNAs, on the other hand, are efficiently labeled by T4 polynucleotide kinase after they have been allowed to react with ATP-γ-S. Furthermore, this labeled RNA can be purified on a thiopyridine-activated thiopropyl sepharose column, demonstrating that the thiophosphate label is not lost during the reaction with ATP and T4 polynucleotide kinase. Thus, the Class IV and VII kinases do not catalyze reactions involving their 5'-hydroxyls.

Conclusive evidence for the 2'-kinase hypothesis is provided by partial alkaline hydrolysis of the auto-thiophosphorylated, 5'-$^{32}$P-labeled RNA. For this analysis, RNA was reacted with ATP-γ-S as described above for TLC analysis, except that 100 µM unlabeled ATP-γ-S was used. The thiophosphorylated RNAs were purified on thiopyridine-activated thiopropyl sepharose, and then 5'-end labeled using T4 polynucleotide kinase and ATP-γ-$^{32}$P. Alkaline hydrolysis was performed in 50 mM sodium carbonate/bicarbonate buffer, pH 9.0, 0.1 mM EDTA for 3 min. at 90° C. Reaction products were analyzed on an 8% polyacrylamide/8M urea gel.

For RNAs from both Classes IV and VII, a gap is seen in the alkaline hydrolysis ladder of the auto-thiophosphorylated material that is not present in the ladder made with unreacted RNA. The missing bands can be most easily explained if the 2'-hydroxyls at these positions are thiophosphorylated, thus preventing base-catalyzed RNA hydrolysis. This experiment permitted identification of positions of thiophosphorylation: G62 in Kin.10 (Class IV) and G83 in Kin.62 (Class VII). G62 is in a putative helix within the ATP aptamer region of Kin.10, and G83 is in the random loop between the two halves of Kin.62's aptamer domain.

Kinetic Analysis of Kinase Ribozymes

Kinetic analysis of the most active clone from each of the four major classes of kinases has revealed that they all obey the standard Michaelis-Menten kinetics expected of molecules possessing saturable substrate binding sites. Rates for each clone were determined (as described herein) at 6 different ATP-γ-S concentrations, ranging from 2 µM–2.5 µM. Values of $k_{cat}$ and $K_m$ are shown in Table 1, and range between 0.03 and 0.37 min$^{-1}$ and between 41 and 456 µM, respectively.

TABLE 1

| Kinase Class (Clone) | $k_{cat}$ (min$^{-1}$) | $K_m$ (µM) |
|---|---|---|
| Class I (Kin.46) | 0.37 ± 0.01 | 456 ± 57 |
|  | 0.23 ± 0.02 | 116 ± 41 |
|  | 0.36 ± 0.02 | 352 ± 85 |
| Class II (Kin.25) | 0.20 ± 0.02 | 41 ± 15 |
|  | 0.33 ± 0.02 | 42 ± 11 |
| Class III (Kin.42) | 0.07 ± 0.005 | 50 ± 13 |
|  | 0.10 ± 0.016 | 58 ± 28 |
| Class IV (Kin.44) | 0.03 ± 0.001 | 276 ± 25 |
|  | 0.03 ± 0.001 | 200 ± 22 |

The $k_{cat}$ for Class I–IV ribozymes compares favorably with corresponding values for naturally occurring ribozymes, which range from 0.04 to 2 min$^{-1}$. Comparison of $k_{cat}/K_m$ is difficult because most natural ribozymes have oligonucleotide substrates that form base pairs with the ribozyme's substrate binding site, leading to very low $K_m$ values. A comparison between the kinase ribozymes described here and the self-cleavage reaction catalyzed by the Tetrahymena Group I intron is particularly relevant, however, because both reactions use external small molecule substrates (ATP-γ-S and guanosine nucleotides, respectively) to modify themselves. Kin.25 (Class II) phosphorylates itself with a $k_{cat}$ of approximately 0.3 min$^{-1}$ and a $k_{cat}/K_m$ of 6×10$^3$ min$^{-1}$M$^{-1}$. The Tetrahymena self-splicing intron has a $k_{cat}$ of 0.5 min$^{-1}$ and a $k_{cat}/K_m$ of 2.5×10$^4$ min$^{-1}$M$^{-1}$ (Bass and Cech, *Nature* 308:820, 1984). Thus, from a vanishingly small sampling of sequence space, it has been possible to isolate a molecule with autocatalytic activity essentially as good as that of a ribozyme found in nature.

Class I–IV kinases show specificity for ATP-γ-S as a substrate. No reaction (<0.1% ATP-γ-S rate) could be detected with GTPγS, indicating that the RNAs can discriminate between similar substrates. Interestingly, as much as 30% of the cycle 13 pool RNA can use GTP-γ-S as a substrate, and thus pool 13 does contain molecules with less stringent substrate specificities. The Class I–IV kinases are also able to discriminate between ATP-γ-S and ATP ($k_{obs}$ (ATP-γ-S)/$k_{obs}$ (ATP): Class I=55; Class II=300; Class III=150; Class IV≥300; 100 µM ATP, ATP-γ-S). Since these values are significantly larger than the three to ten fold intrinsic reactivity difference between ATP-γ-S and ATP (Herschlag et al., *Biochemistry* 30:4844, 1991), the data suggest that the thiophosphate is important for binding, catalysis or both. Furthermore, pool 13 RNA is not detectably labeled by either ATP-α-$^{35}$S or ATP-α-$^{32}$P, suggesting that 5' splicing is not a reaction that occurs in the pool (unless the γ-thiophosphate is an absolute requirement for the molecules that carry out this reaction). Rate Acceleration: The uncatalyzed background reaction for the thiophosphorylation of RNA (or guanosine) by ATP-γ-S was not detectable. Based on the sensitivity of these experiments, the lower limit for the rate acceleration of the kinase ribozymes is roughly 10$^5$-fold. At 70° C. the rate of hydrolysis of ATP in the presence of Mg$^{2+}$ is ~4×10$^{-4}$ min$^{-1}$ (pH 6–8). Correcting for the temperature and 55M water, this value gives a second order rate constant of approximately 1×10$^{-6}$ min$^{-1}$M$^{-1}$. ATP-γ-S should hydrolyze 3–10 times faster than ATP. Taking this factor into account, the approximate rate enhancement of the present ribozymes $[k_{cat}/K_m]/[k_{hydrolysis}]$, would be $6 \times 10^3$ min$^{-1}$M$^{-1}$/$\sim 10^{-5}$ min$^{-1}$M$^{-1}$ or $10^8$–$10^9$ fold. This enhancement corresponds to an effective molarity of $10^4$–$10^5$M for ATP in the ATP-ribozyme complex ($k_{cat}/k_{hydrolysis}$=0.3 min$^{-1}$/$10^{-5}$ min$^1$ M$^{-1}$). A comparison of first-order rate constants gives a value for the rate enhancement that is independent of substrate binding. This value is approximately $10^3$ fold ($k_{cat}/k_{hydrolysis}$ (1° order)=0.3 min$^1$/ $\sim 4 \times 10^{-4}$ min$^{-1}$). This analysis assumes that the mechanism of hydrolysis of ATP-γ-S (dissociative) is the same as that used by the kinase ribozymes.

Intermolecular Catalysis and Turnover

At least one of the selected kinases is capable of catalyzing the phosphorylation of a separate RNA substrate. In particular, Kin.46 (Class I) was demonstrated to transfer the γ-thiophosphate from ATP-γ-S to the 5'-end of a 6-mer oligoribonucleotide with the same sequence as the 5'-end of the ribozyme. To carry out this experiment, RNA was incubated as described in FIG. 2 except that 2.5 mM ATP-γ-S was used, and 100 µM 5'-HO-GGAACC-3' RNA was added. The 6-mer was synthesized by run-off transcription (Milligan et al., Meth. Enzymol. 180:51, 1989) and was dephosphorylated with calf intestinal alkaline phosphatase prior to ion-exchange HPLC purification. The thiophosphorylated 6-mer marker was made by end-labelling 5'-GGAACC-3' with ATP-γ-$^{35}$S using T4 polynucleotide kinase. Products were analyzed on 20% acrylamide/8M urea gels. Full-length Kin.46 was found to catalyze the reaction approximately 500-fold more slowly than the autocatalytic reaction. Part of the reason for the decreased activity is likely to be competition for the active site between the 5'-end of the RNA and the exogenous 6-mer substrate. When the 5'-constant region of the RNA is removed (via PCR with an internal 5'-primer, followed by transcription), the activity increases ~100-fold, but is still 6 fold below that of the auto-thiophosphorylation reaction. (At saturating concentrations of 6-mer (100 µM) and ATP-γ-S (2.5 mM) the initial rate of thiophosphorylation is 0.05 µM/min with 1 µM ribozyme. In comparison, the rate of auto-thiophosphorylation for full length Kin.46 RNA (1 µM) with 2.5 mM ATP-γ-S is 0.3 µM/min.) At 25° C. the ribozyme performs approximately 60 turnovers in 24 hours, and is thus acting as a true enzyme. The cause of the lower trans activity relative to the autocatalytic activity remains unknown, but could involve slow substrate binding or improper folding of the shortened ribozyme. The off rate of the 6-mer is not limiting because no burst phase is observed in a time course of the reaction.

The identification of autocatalytic ribozymes capable of carrying out catalysis in trans, i.e., catalyzing a reaction involving the ligand and a molecule other than the ribozymes itself can be found by testing the ability of the ribozyme to act on a molecule having a sequence similar to the region of the ribozyme which is modified.

Figure 7A:
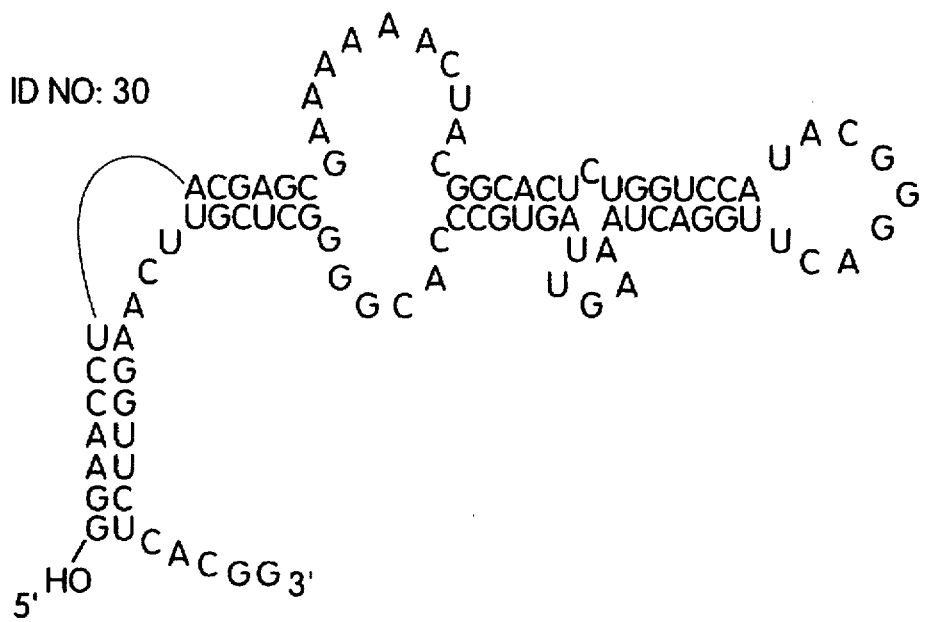
FIG. 7A is a schematic illustration of a ribozyme capable of transferring a phosphate to its 5' end (SEQ ID NO:30).
Figure 7B:
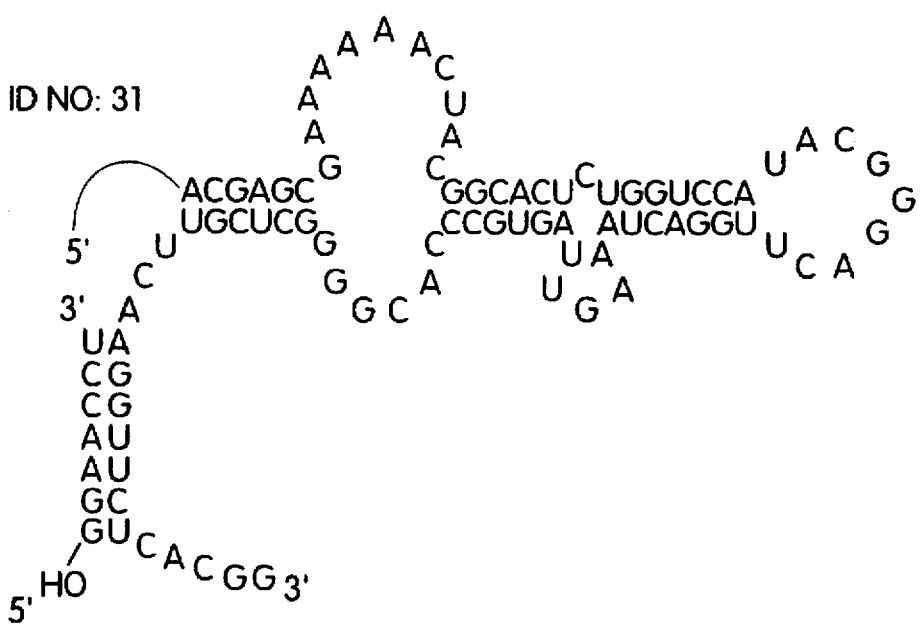
FIG. 7B is a schematic of a trans-acting ribozyme and a substrate (GGAACCU).

FIG. 7A illustrates an example of a cis-acting ribozyme with polynucleotide kinase activity. A ribozyme capable of carrying out this catalysis in trans can be made by eliminating the 5' end of the ribozyme which would otherwise base pair with the 3' end of the ribozyme and be kinased. The particular molecule shown in FIG. 7B is derived from the moleucle illustrated in panel FIG. 7A and transfers phosphate to the 5' end of the short oligoribonucleotide GGAACCU.

EXAMPLE 2

Figure 8C:
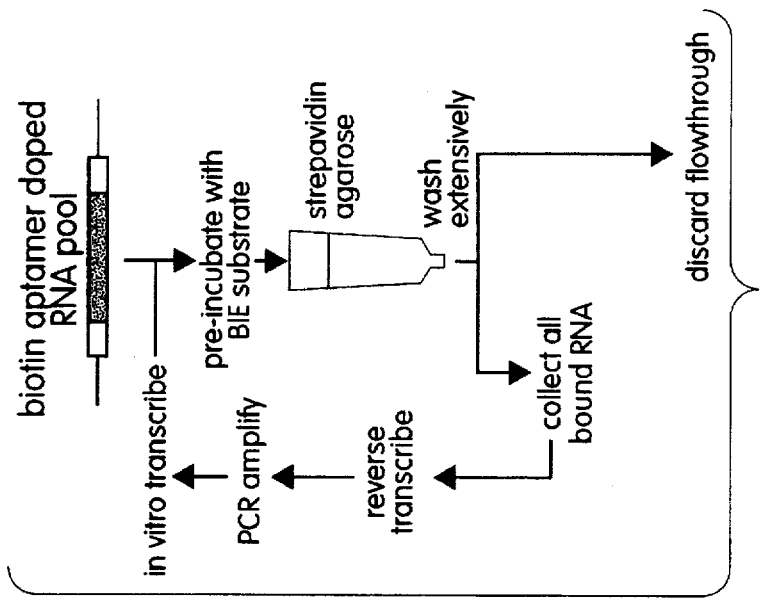
FIG. 8C is a scheme for isolating self-biotinylating RNA enzymes.
Figure 8B:
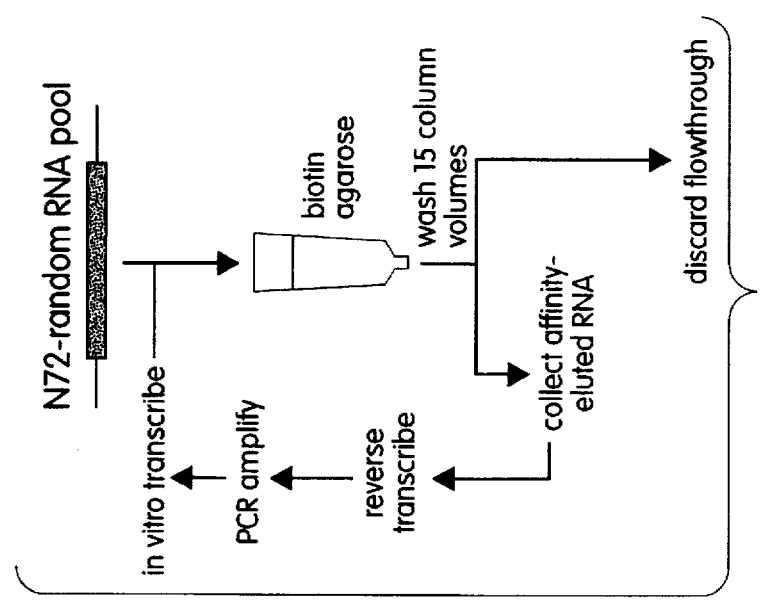
FIG. 8B is a scheme for isolating biotin-binding RNAs by affinity chromatography.
Figure 8A:
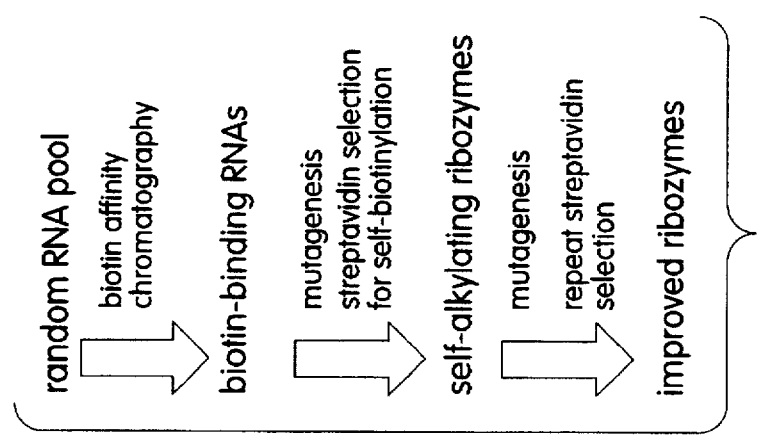
FIG. 8A is a strategy for in vitro evolution of self-alkylating ribozymes.

In a second example of the invention, RNAs which bind biotin were first created, identified, and isolated using a randomized RNA pool. The selected RNAs were used to prepare a second pool of partially randomized RNAs. This pool was then subjected to selection and amplification to identify RNAs capable of ligating biotin. The overall scheme is illustrated in FIGS. 8A, 8B, and 8C.

Selection of biotin-binding RNAs

A pool of approximately $5 \times 10^{14}$ different random sequence RNAs was generated by in vitro transcription of a DNA template containing a central 72-nucleotide random sequence region, flanked at both ends by 20-nucleotide constant regions. This pool (random N72 pool) had the following sequence: GGAACACTATCCGACTGGCA(N)$_{72}$CCTTGGTCATTAGGATCG (SEQ ID NO:3) (FIG. 8D, also SEQ ID NO:32). On average, any given 28 nucleotide sequence has a 50% probability of being represented in a pool of this complexity. The initial pool of RNA (approximately 80 µg; on average, 2–3 copies of each sequence) was resuspended in a binding buffer containing 100 mM KCl, 5 mM MgCl$_2$, and 10 mM Na-HEPES, pH 7.4, conditions chosen to favor RNA folding and to mimic physiological environments while minimizing non-specific aggregation. The solution was applied to an agarose column derivatized with 2–6 mM biotin (Sigma, St. Louis, Mo.) and subsequently washed with 15 column volumes of binding buffer. Specifically-bound RNAs were then eluted by washing the column with binding buffer containing 5 mM biotin. Ten µg of glycogen and 0.3M NaCl were then added to the eluted material, and the RNA was amplified as follows. Briefly, the mixture was precipitated with 2.5 volumes of ethanol at −78° C. After resuspending the selected RNA, the reverse transcriptase primer (2.5 µM) was annealed at 65° C. for 3 min., and reverse transcription (RT) was carried out at 42° C. for 45 min. (using Superscript RT enzyme, Life Technologies, Inc.). PCR amplification was performed by diluting one-fifth of the RT reaction with the appropriate dNTPs, PCR buffer, USB Taq polymerase (United States Biochemical, Cleveland, Ohio), and 0.5 µM (+) primer containing the T7 RNA polymerase promoter. A strong band of the correct size was typically observed after 8–15 cycles amplification (94° C., 1 minute; 55° C., 45 seconds; 72° C., 1 minute). Half of the PCR reaction was used for in vitro transcription with T7 RNA polymerase (37° C., overnight). The resulting RNA was purified by electrophoresis on an 8% polyacrylamide gel.

Figure 9B:
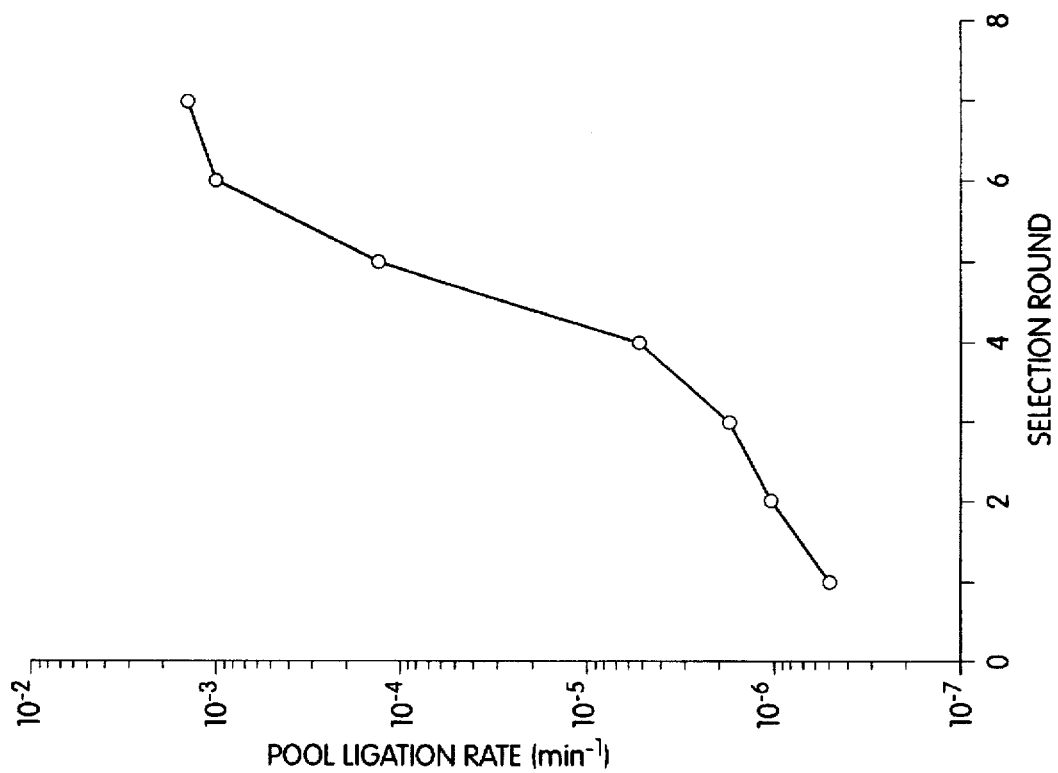
FIG. 9B illustrates progress of the self-biotinylation selection. Ligation rate determined by incubation with 200 µM BIE followed by streptavidin-agarose purification. Values are corrected for 0.02% non-specific RNA binding.
Figure 9A:
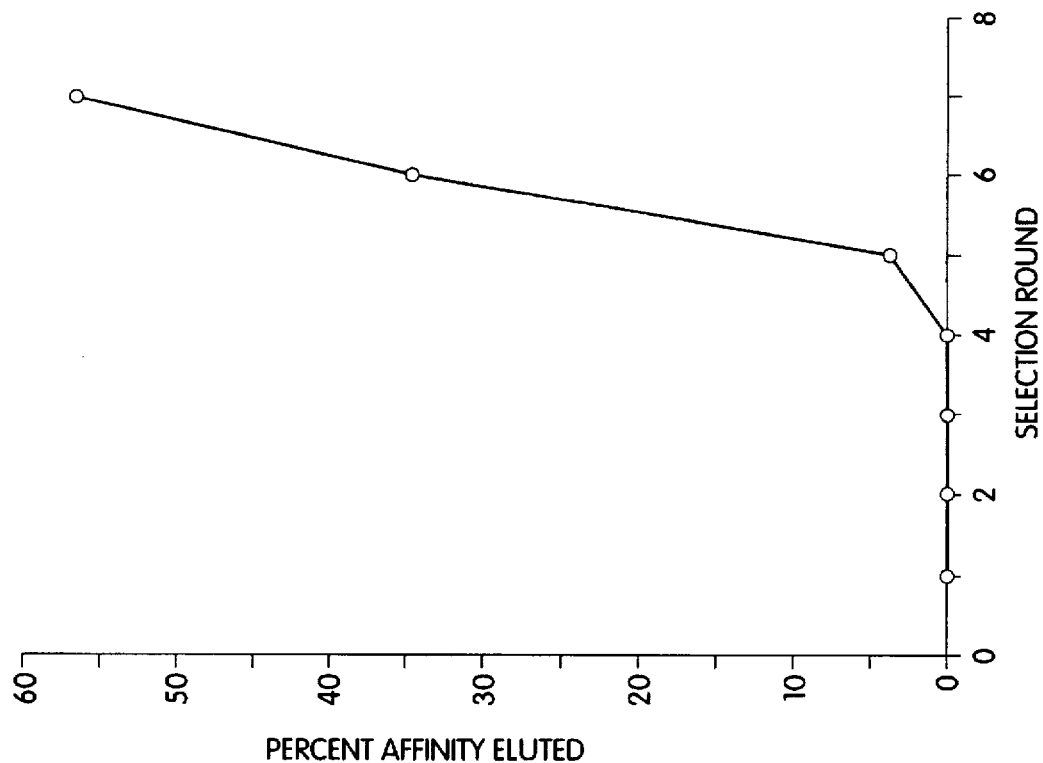
FIG. 9A illustrates progress of the biotin aptamer selection. Biotin-eluted RNA expressed as a percentage of total RNA applied to the biotin-agarose column is plotted as a function of selection cycle. Individual RNAs eluted from the seventh round were subcloned and sequenced. Greater than 90% of the clones correspond to the sequence shown in FIG. 12.

After six rounds of repeated enrichment, more than half of the RNA applied to the biotin column was retained during the buffer wash, but eluted during the biotin wash (FIG. 9A). The RNA pool from the eighth round of selection was cloned into the pCR vector using the TA cloning kit (In Vitro-Gen, Inc., San Diego, Calif.), and individual aptamers were sequenced by the Sanger dideoxynucleotide method using the universal M13 primer. A single sequence (represented by clone BB8-5) accounted for ≧90% of the selected pool (two minor clones account for the vast majority of remaining RNAs).

Previous RNA selections for binding to small ligands, including various dyes, amino acids, cofactors, and nucleotides, have suggested that aptamers exist at a frequency of $10^{-10}$ to $10^{-11}$ in random sequence pools. All of these ligands, however, have contained aromatic rings which could intercalate between RNA bases and/or charged groups which might interact electrostatically with the RNA backbone. The lower frequency of biotin bindings ($10^{-15}$) shows that ligands lacking such groups may require a more complex binding site.

Selection for biotin-utilizing ribozymes

The sequence of the biotin aptamer was used to direct the synthesis of a second pool of RNAs which was screened for the presence of biotin-utilizing ribozymes (FIG. 8A). This pool contained a core of 93 nucleotides (71 nucleotides derived from the original random region plus its 22 nucleotide 5' constant region; FIG. 8D) with the wild-type nucleotide (i.e., that which was found in the original biotin aptamer incorporated at each position in the template with 70% probability (the three non-native nucleotides each occurring with 10% probability). Deletion analysis indicated that the 3' primer was not required for binding and the same sequence was therefore used for the 3' primer of the partially-randomized pool. To allow for the possibility that the 5' primer formed part of the aptamer core, the original 5' primer sequence was included in the partially-randomized region of the new pool and a different 5' primer was appended for amplification. Because of differences in the relative rates of phosphoramidite incorporation during DNA synthesis, a biased mix of all four nucleotides was prepared with molor ratios of 3:3:2:2 (A:C:G:T). This mix was added to pure phosphoramidite stocks (A and C: 64% pure stock, 36% random mix; G and T: 55% pure stock, 45% random mix) to yield mixed stocks for pool synthesis.

Twelve random bases were added to either end of this core sequence and new constant primers for PCR amplification were included. The synthesis of this 156 nucleotide DNA sequence yielded a pool containing $8 \times 10^{13}$ different molecules, which were transcribed to yield a pool of RNA molecules clustered in sequence space around the original biotin aptamer sequence. The total yield from the DNA synthesis was approximately 77 µg (1.52 nmole). The quality of the synthetic DNA was determined by a primer extension assay, which showed that only 8.7% of the DNA molecules could serve as full length templates for Taq polymerase. The pool thus contains $1.52 \times 10^{-9} \times 6.02 \times 10^{23} \times 0.087 = 8 \times 10^{13}$ distinct sequences.

This second RNA pool was used to identify ribozymes able to enhance the rate of self-alkylation with the haloacetyl derivative, N-biotinoyl-N'-iodoacetylethylenediamine (BIE; Molecular Probes, Eugene, Oreg.). BIE is normally used to biotinylate proteins by reaction with free cysteine sulfhydryls. To provide one potential internal substrate for the alkylation reaction, the doped pool was transcribed in the presence of excess 8-mercaptoguanosine, thus yielding RNAs containing a single free thiol in the 5'-terminal nucleotide. Following an overnight (15 hour) room temperature incubation with 200 µM BIE, RNAs that had undergone the self-biotinylation reaction were isolated by streptavidin agarose chromatography.

In particular, reaction with BIE was terminated by the addition of 100 mM β-mercaptoethanol, 5 mM EDTA, 0.3M NaCl, 50 µg tRNA (E. coli, RNAse-free, Boehringer-Mannheim, Indianapolis, Ind.). After five minutes, the mixture was precipitated with 2.5 volumes ethanol on dry ice. After washing and resuspension, the RNA was applied to 0.5 ml of a 50% slurry of streptavidin agarose in wash buffer (1M NaCl, 10 mM NaHepes, pH 7.4, 5 mM EDTA) that had been washed with 50 µg tRNA. After rocking 30 minutes to allow streptavidin-biotin binding, the mixture was transferred to a 10 ml-column and washed with 4×10 ml wash buffer and 2×10 ml distilled water.

RNA bound to streptavidin could be affinity eluted by first saturating the free biotin-binding sites with excess biotin and then heating in the presence of 10 mM biotin at 94° C. for 8 minutes. Amplification of the resultant molecules (by reverse transcription, PCR, and transcription) yielded a pool enriched for catalysts.

After three rounds of selection, an increase in the proportion of RNAs binding to the streptavidin was observed (FIG. 9B). By the fifth round, 10% of the RNA ligated the biotin substrate. To select for the most active catalysts, the incubation time was progressively shortened from 15 hours to 30 minutes to 1 minute. After eight rounds of selection, no further increase in activity was observed suggesting that the complexity of the starting pool had been exhausted. Sequencing individual clones from the selected pool showed that 50% of the ribozymes were very closely related and were derived from a single progenitor. One of these clones, BL8-6, catalyzes self-biotinylation at a rate of 0.001 min$^{-1}$ in the presence of 200 µM BIE.

The rate of self-biotinylation was determined by a time course experiment. $^{32}$P-labelled RNA was first resuspended in incubation buffer (100 mM KCl, 10 mM Na-Hepes, pH 7.4, 5 mM MgCl$_2$) and allowed to equilibrate for 10 minutes at room temperature. 200 µM BIE was added to the mixture and aliquots were subsequently removed after 0 to 120 minutes of incubation. Samples were quenched and affinity purified as described in Haugland, Molecular Probes Handbook of Fluoprescent Probes and Research Chemicals. Aliquots were counted in a scintillation counter following ethanol precipitation (total RNA count) and following binding to streptavidin agarose (product RNA count); the ratio of these two counts is the fraction reacted. Optimizing enzymatic activity: It seemed likely that the original RNA pool from which the BL8-6 ribozyme was derived might not saturate the space of biotin-ligating ribozymes. To test the possibility that appropriate additional mutations to the BL8-6 sequence might increase its catalytic activity, a third RNA pool was generated based on its sequence but with non-wild-type nucleotides substituted at each position with 30% probability (FIG. 8D) (using methods described above). The selection for catalytic activity was repeated as described above, but with both the reaction incubation time and the BIE concentration progressively lowered to select for the most active enzymes. After eight rounds of selection (ending with a 1 minute incubation period at 10 µM BIE), active clones from the pool were sequenced and assayed for catalytic activity. Ribozymes in this pool were uniformly more active than their BL8-6 progenitor, with one clone (BL2.8–7) catalyzing self-biotinylation at a rate of 0.05 min$^{-1}$ in the presence of 100 µM BIE (one hundred fold more active than BL8-6).

Nature of the reaction product.

Figure 10A:
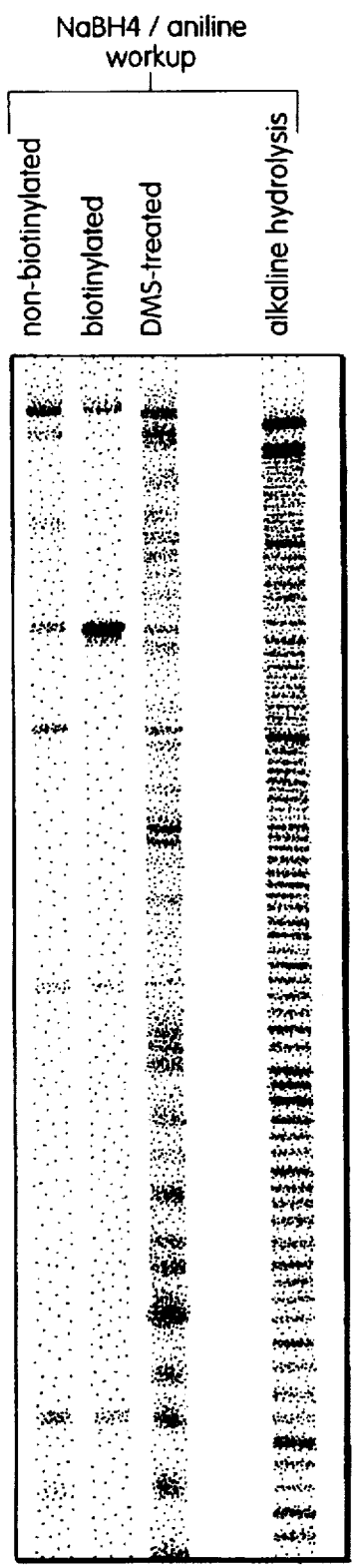
FIG. 10A is a site-specific alkylation reaction catalyzed by BL8-6 ribozyme. 5'-end labeled BL8-6 RNA was allowed to react overnight with 200 µM BIE and then separated by streptavidin affinity chromatography into biotinylated and non-biotinylated fractions. RNA was then treated with sodium borohydride and aniline acetate to specifically cleave at N7 alkylation sites. For comparison, DMS-treated RNA was treated in parallel. A single major cleavage site in the biotinylated fraction (corresponding to Gua-96) is absent from the non-biotinylated RNA. Minor bands present in the non-biotinylated fraction appear to result from non-specific RNA cleavage as judged by their greater intensity in BL8-6 RNA subjected to partial alkaline hydrolysis.

The observation that BL8-6 ribozyme transcribed without 8-mercaptoguanosine catalyzed the self-biotinylation reaction as efficiently as the thiol-containing RNA indicated that some site other than the free thiol in the 8-mercaptoguanosine base at the 5'-end of the RNA might serve as nucleophiles for the alkylation reaction. However, the observation that BL8-6 ribozyme transcribed without 8-mercaptoguanosine catalyzed the self-biotinylation reaction as efficiently as the thiol-containign RNA indicated that some other site was being alkylated. To identify the reactive site, 5'-end labelled BL8-6 ribozyme that had reacted with BIE was subjected to alkaline hydrolysis, and the resultant ladder of molecules was affinity purified on streptavidin agarose. In particular, RNA was partially hydrolyzed by heating to 90° C. for 7 minutes in the presence of 100 mM NaHCO$_3$, pH 9.0 and subsequently ethanol precipitated. After resuspending in wash buffer, biotin-labelled RNA was affinity purified as described by Haugland (supra). Purified non-biotinylated RNA was obtained from the initial flowthrough fraction from the streptavidin agarose slurry (prior to washing). Full length RNAs and those with the approximately 60 3'-terminal nucleotides deleted were retained by the streptavidin whereas shorter molecules were not bound. This result maps the biotin attachment site to the region . . . 5'-$^{92}$GGACGUAAA$^{100}$-3' . . . Alkylation at the N7 position of purines leads to RNA strand scission following treatment with sodium borohydride followed by aniline acetate (this reaction serves as the basis for the RNA chemical sequencing) (Peattie, *Proc. Natl. Acad. Sci. USA* 76:1760, 1979). RNA incubated with BIE, purified on streptavidin-agarose, and treated in this manner was cleaved at G$^{96}$ ( . . . GGACGUAAA . . . ) (FIG. 10A). Briefly, RNA was dissolved in 1.0M Tris-HCl, pH 8.2 and 0.2M NaBH$_4$. Following a 30 min. incubation, the reaction was quenched with 0.6M sodium acetate/0.6M acetic acid, pH 4.5, containing carrier tRNA. Following precipitation and rinsing, the RNA was treated with 1.0M aniline/acetate, pH 4.5 at 60° C. for 20 min. No G$^{96}$-specific cleavage was observed for RNA that had been exposed to BIE but not biotinylated (i.e. the streptavidin flowthrough fraction). G$^{96}$ is therefore the alkylation site for the ribozyme.

Figure 10B:
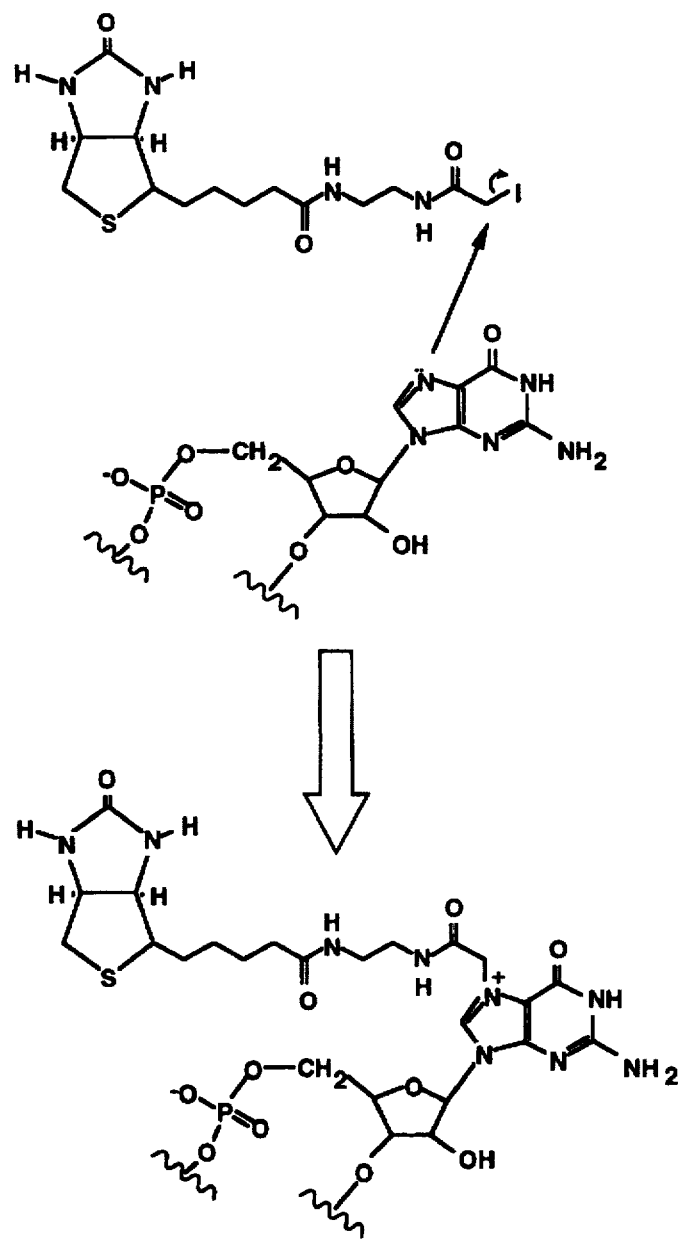
FIG. 10B illustrates the inferred N-alklyation reaction at the N7 position of G-96

To further characterize the alkylation product, the BL8-6 ribozyme was transcribed with [α-$^{32}$P]-GTP, thus labelling phosphates attached to the 5'-hydroxyl of all guanosines in the RNA. Following reaction with BIE, biotinylated RNA was streptavidin-purified and subsequently digested to 5'-monophosphate nucleotides with snake venom phosphodiesterase I. Labelled RNA was diluted with 25 μL 10 mM NaCl, 10 mM MgCl$_2$, 10 mM Tris-Cl, pH 7.4, and 5 μL phosphodiesterase I (Boehringer-Mannheim, Indianapolis, Ind.) and incubated for 20 hrs at 37° C. Thin layer ion exchange chromatography was carried out by spotting plates pre-run with water to remove excess salts and then developed with 6 M formic acid. The PEI cellulose plates (J. T. Baker Co., Phillipsburg, N.J.) indicated the presence of a radioactive species in the streptavidin-purified RNA that was absent from the streptavidin-flowthrough RNA. This adduct migrated more rapidly than 5'-GMP in this TLC system, and co-migrated with 7-methyl GMP, suggesting that the adduct carries a positive charge, consistent with alkylation at N7 (FIG. 10A and FIG. 10B). Although the possibility of alkylation at N1 or N3 cannot be ruled out, alkylation at either of these sites would not be expected to lead to strand cleavage following aniline treatment, but would be expected to disrupt reverse transcription, thus preventing catalysts using these nucleophiles from being enriched during the in vitro selection procedure. Taken together, these results strongly suggest that N7 of G$^{96}$ is the alkylation site.

The catalyzed rate enhancement

The background rate of guanosine alkylation by BIE was determined by two independent methods. First, radiolabelled random sequence RNA (from the pool used to isolate the original biotin binder) was incubated for 24 hours with or without 200 μM BIE. The specstreptncrease in the fraction bound by streptavidin agarose (0.15%) after extensive washing was taken as a measure of the background reaction. Assuming an average of 28 guanosines/RNA sequence, this fraction corresponds to a non-catalyzed alkylation rate of 2.3×10$^{-6}$ s$^{-1}$M$^{-1}$. In a similar approach, low concentrations of [α-$^{32}$P]-GTP were incubated overnight in the presence or absence of 200 μM BIE and after 12 hours, affinity purified by streptavidin agarose. The fraction specifically bound (3.4×10$^{-5}$) indicates a non-catalyzed rate of 2.3×10$^{-6}$ s$^{-1}$M$^{-1}$, in close agreement with that obtained from the RNA labelling experiment. A time course experiment with BL2.8-7 RNA yields a catalyzed biotinylation rate of approximately 8s$^{-1}$M$^{-1}$. The ribozyme rate enhancement is thus approximately 3×10$^6$, comparable to that of the most active catalytic antibodies although substantially less than that of many natural protein enzymes (Tramontano et al., *J.*

*Am. Chem. Soc.* 110:2282, 1988; Janda et al., *ibid.* 112:1275, 1990). Structural differences between the biotin binder and the biotin ligator: Given that the biotin ligator arose by mutagenesis of the biotin binder sequence and that both molecules interact specifically with biotin, we expected to find significant structural similarities between the two RNAs. Simple comparison of their primary sequences, however, failed to identify a well-conserved domain that might play a functional role; mutations appear randomly distributed along the length of the two sequences. To characterize the functional cores of the two molecules, we analyzed the sequences of active clones isolated from the two mutagenized RNA pools generated from the biotin aptamer and self-alkylating ribozyme sequences. After four rounds of reselection with the biotin aptamer-derived pool, >40% of the applied RNA bound tightly to biotin agarose. Similarly, three rounds of re-selection of the self-alkylating ribozyme-derived pool yielded a collection of RNAs with activity matching that of the original BL8-6 clone, and five additional rounds of selection increased the activity ~100-fold. Approximately thirty individual RNAs from each of these subcloned pools were sequenced and analyzed to determine which nucleotide positions were conserved and which pairs of nucleotides covaried to maintain Watson-Crick base pairing. The results of these experiments are summarized below and in FIGS. 11, FIGS. 12A, and 12B.

Figure 12A:
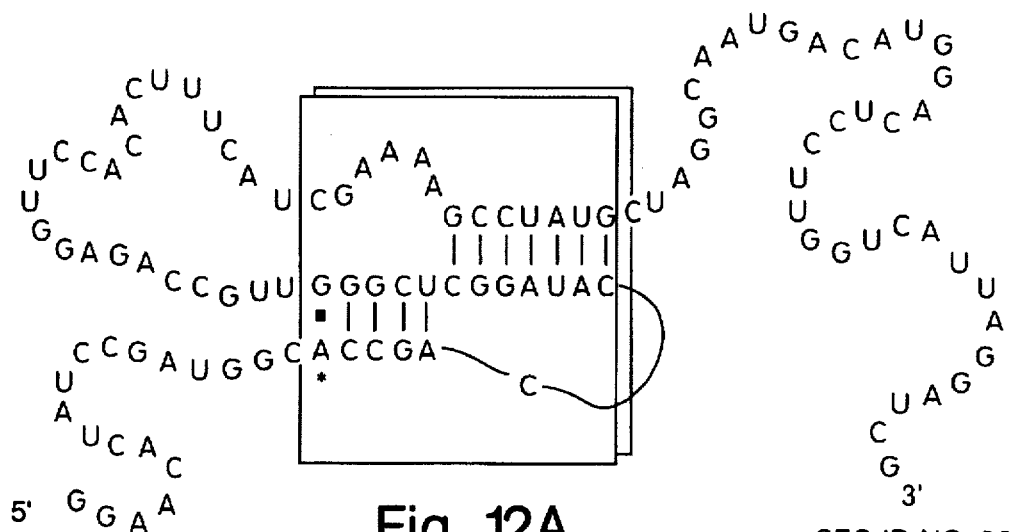
FIG. 12A and 12B illustrates the proposed secondary structures for the biotin aptamer and the self-biotinylating ribozyme. Nucleotides within the boxed region are highly conserved and make up the essential core of the aptamer and ribozyme. Asterisks indicate pairs of positions that co-vary in a Watson-Crick sense. Nucleotides in the constant primer sequences are shown in italics.

Two regions of the biotin binder are very highly conserved in clones that retain binding activity (FIG. 11). Mutations at the 5' and 3' ends of the first conserved domain (changing the A$^{53}$.G$^{70}$ pair to either C:G or A:T) suggest a hairpin structure stabilized by a 4-base-pair Watson-Crick duplex. Seven non-paired bases in the middle of the first domain directly complement the 3'-terminal half 5 of the second conserved domain, thus suggesting a pseudoknot structure (FIG. 12A). In that the bases in these conserved domains are essentially invariant, the sequence data provide no covariational evidence for the pseudoknot. To test the proposed structure, a series of site-directed mutants was generated and assayed for binding to biotin agarose. Single-base substitutions that disrupt proposed Watson-Crick base pairs in the pseudoknot completely abolish biotin binding while compensatory second site mutations that introduce non-native Watson-Crick base pairs are able to largely restore biotin binding. These data strongly support the proposed pseudoknot model for the biotin aptamer.

Comparison of the sequences of active ribozymes from the BL8-6 re-selection indicate a striking change in structure relative to the original biotin binder. Nucleotides involved in the pseudoknot base-pairing (53–70, 101–107), virtually invariant in the biotin binders, are poorly conserved in the enzyme sequences (FIG. 11). In contrast, the ribozyme sequence in the region corresponding to the variable connecting loop of the biotin binder (nucleotides 71 to 94) appears to be well conserved, suggesting a structural role. Nucleotides that are very highly conserved in the biotin binder but not involved in the pseudoknot base pairing ( . . . 5'-$^{95}$CGAAAAG$^{101}$-3' . . . ) are retained in the self-alkylating enzymes but with a highly conserved change to . . . 5'-$^{95}$CGUAAAG$^{101}$-3' . . . These results suggest that the change in function from biotin binding to alkylation of RNA with BIE is achieved by major structural rearrangements.

Figure 12B:
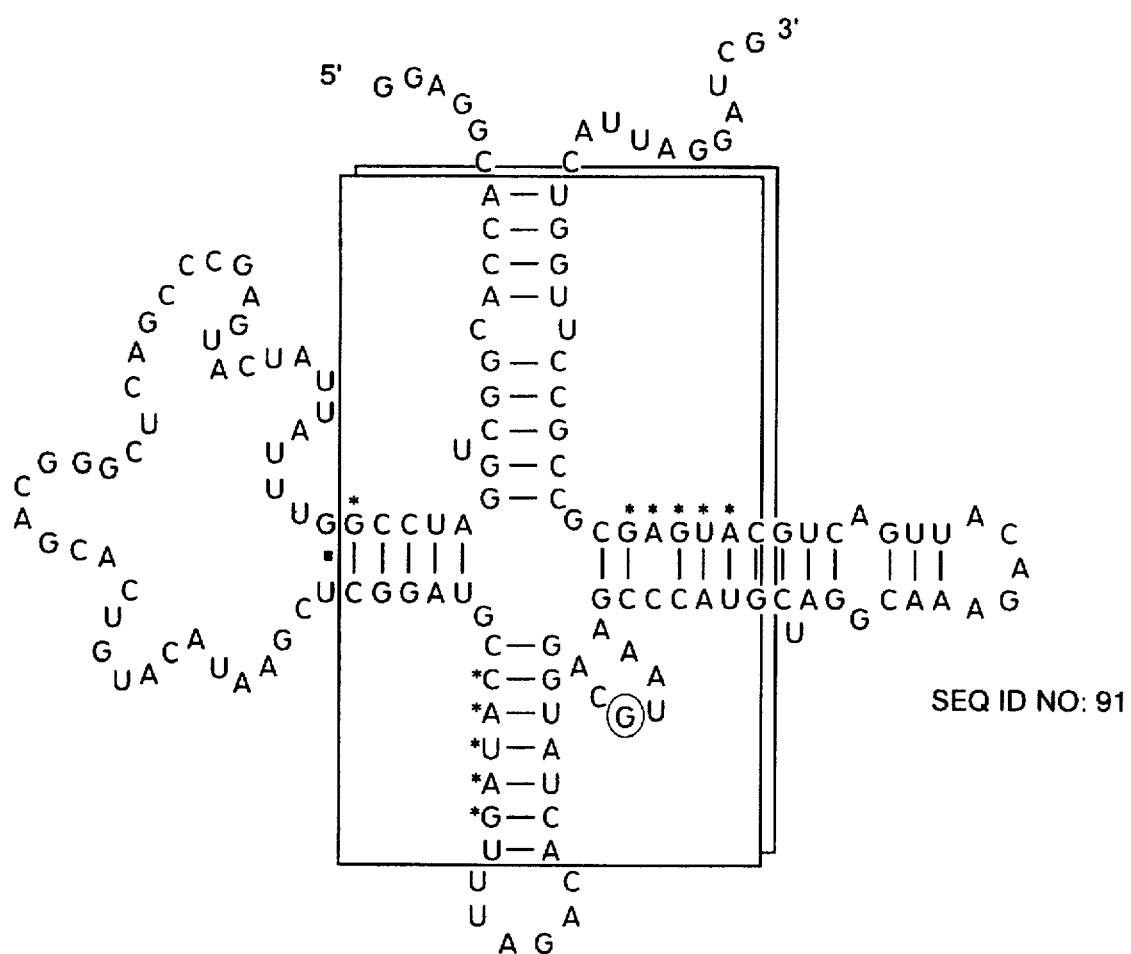

Further analysis of the BL8-6-derived sequences suggested a cloverleaf structure with several remarkable similarities to tRNA (FIG. 12B). The sequence . . . 5'-$^{94}$ACGUAAA100-3' . . . is presented as the tRNA variable stem, flanked on either side by extended duplexes (as indicated by several observed Watson-Crick covariations).

The single guanosine in the variable stem serves as the internal alkylation site for the enzyme. One interpretation of these results is that the hexanucleotide segments CGAAAA and CGUAAA directly mediate the interaction with biotin in the biotin binder and the biotin ligator respectively, although they are presented in strikingly different secondary structure contexts. Comparison of ribozyme sequences from the third and eighth rounds of reselection suggest that the increase in pool alkylation activity is achieved by optimization of Watson-Crick base pairing in the cloverleaf duplexes and an increased fraction of purines (particularly adenosine) in the loop that caps helix 3.

Figure 13B:
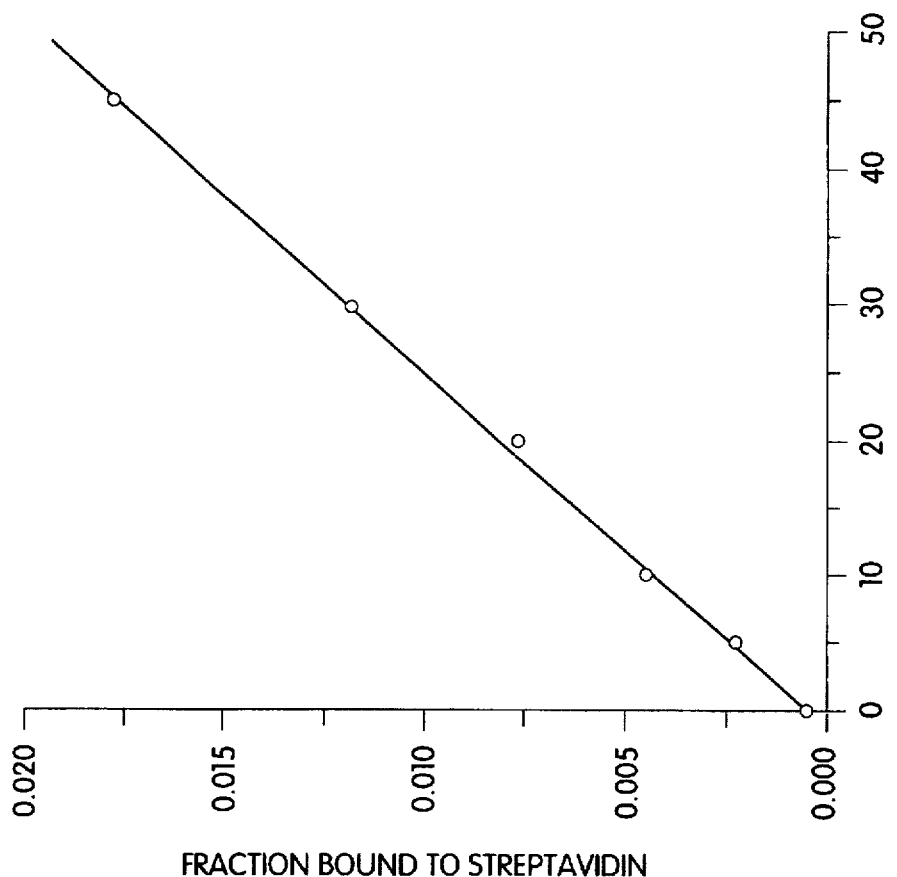
FIG. 13B illustrates in vitro transcribed RNA assayed for self-biotinylation with 10 µM BIE. Folding was calculated by the LRNA Program (Zuker, Science 244:48, 1989)
Figure 13A:
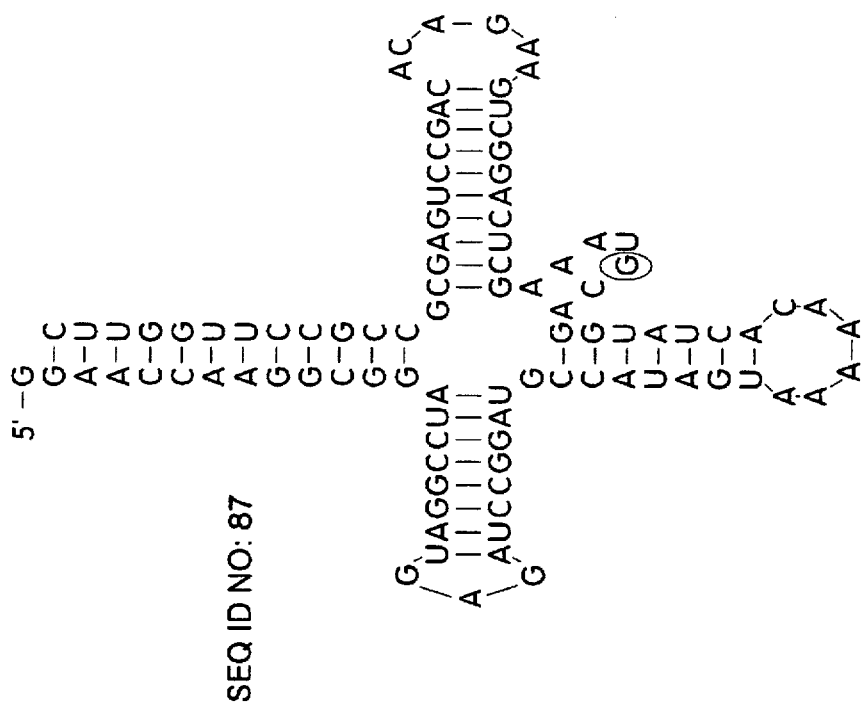
FIG. 13A illustrates the sequence (SEQ ID NO: 87) of a clone obtained from the partially-randomized ribozyme pool after re-selecting for biotinylation activity (BL2.8-9) was modified to allow folding into an idealized cloverleaf structure.

To test the cloverleaf model for the biotin ligator, a synthetic ribozyme was designed by modifying one of the re-selected sequences such that 1) primer sequences at the 5'- and 3'- ends not involved in the cloverleaf were deleted; 2) non-conserved bulges in the putative helices were removed, and 3) the variable loop of approximately 45 nucleotides was replaced by a three nucleotide loop sequence. The predicted lowest energy structure for the resulting 99-nucleotide molecule is shown in FIG. 13. This highly simplified structure has ~10 fold lower activity than the best re-selected clone, but is still ~10 fold more active than the original BL8-6 ribozyme, thus supporting the proposed cloverleaf structure (FIG. 13).

Two-component ribozyme

Figure 14B:
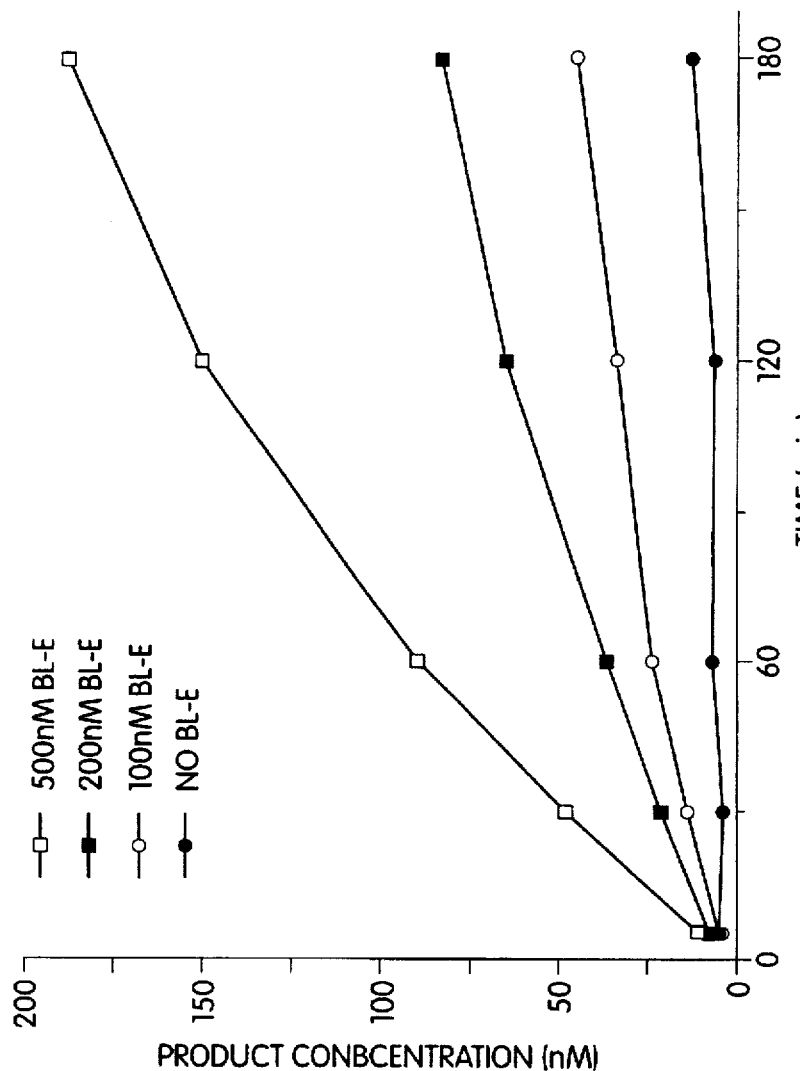
FIG. 14B shows the results of a ribozyme-mediated biotinylation of a separate RNA substrate. The designed self-biotinylating ribozyme (FIG. 13A) was re-engineered into two halves, BL-E and BL-S, that could respectively serve as the enzyme and substrate for the biotinylation reaction. This re-engineered molecule is illustrated in FIG. 14A (SEQ ID NO:88 and SEQ ID NO:89). To assay the two piece system, 5 µM radiolabelled BL-S RNA was incubated in the presence of 200 µM BIE and 0 to 500 nM unlabelled BL-E RNA. RNA biotinylation was determined as described herein. The reaction plateaus overnight at a level corresponding to one equivalent of product.
Figure 14A:
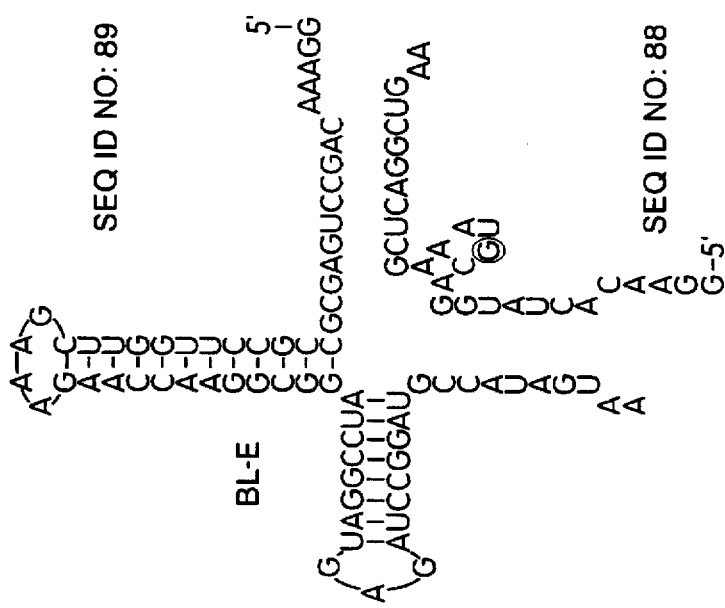

For a ribozyme to properly qualify as an enzyme, it must emerge from the catalyzed reaction unmodified. The self-alkylating ribozyme, which has been selected to covalently modify its own active site, fails to meet this requirement. The cloverleaf secondary structure, however, immediately indicates a way to engineer the ribozyme into two self-associating parts, one of which (BL-S) can function as a substrate for biotinylation while the other (BL-E) acts as a true enzyme (FIG. 14A and FIG. 14B). A low level of BL-S biotinylation, corresponding to the non-catalyzed rate of alkylation was observed in the absence of BL-E. The initial rate of biotinylation of the RNA substrate increased linearly with increasing concentrations of BL-E, although the concentration of product never exceeded the concentration of enzyme. This result indicates that the two RNA pieces can associate with the BIE substrate to form a ternary complex capable of true catalysis. The extensive Watson-Crick base-pairing that drives complex formation most likely prevents dissociation of the biotinylated product and thus limits the enzyme fragment to a single catalytic event. Destabilizing the enzyme-substrate duplexes should make it possible to form a kinetically reversible complex that will dissociate after substrate biotinylation, allowing multiple rounds of turnover.

USE

Nucleic acids produced by the method of the invention can be used as in vitro or in vivo catalysts. In some cases the nucleic acids may be used to detect the presence of the ligand. For example, the nucleic acid may bind the ligand and catalyze a reaction which converts the ligand into a readily detectable molecule. The ribozymes created by the method of the invention can also be used in assays to detect molecules modified by the ribozymes which are not themselves ligands, e.g., an RNA phosphorylated by a polynucleotide kinase ribozyme.

---

SEQUENCE LISTING ( 1 ) GENERAL INFORMATION:

( i i i ) NUMBER OF SEQUENCES: 91

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

GGAACCUCUA GGUCAUUAAG A        21

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

ACGUCAGAAG GAUCCAAG        18

( 2 ) INFORMATION FOR SEQ ID NO:3:

( i ) SEQUENCE CHARACTERISTICS:
        ( A ) LENGTH: 110 base pairs
        ( B ) TYPE: nucleic acid
        ( C ) STRANDEDNESS: single ( D ) TOPOLOGY: linear ( x i ) SEQUENCE DESCRIPTION: SEQ ID NO:3:

| GGAACACTAT | CCGACTGGCA | NNNNNNNNNN | NNNNNNNNNN | NNNNNNNNNN | NNNNNNNNNN | 60 |
| NNNNNNNNNN | NNNNNNNNNN | NNNNNNNNNN | NNCCTTGGTC | ATTAGGATCG | | 110 |

( 2 ) INFORMATION FOR SEQ ID NO:4:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

| GGUGGGAAGA | AACUGCAGCU | UCGGCUGGCA | CC | | | 32 |

( 2 ) INFORMATION FOR SEQ ID NO:5:

( i ) SEQUENCE CHARACTERISTICS:
        ( A ) LENGTH: 134 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

| NNNNNNNNNN | NNNNNNNNNN | NNNNNNNNNN | NNNNNNNNNN | CGAGGGAAGA | AACUGCGGCA | 60 |
| CCNNNNNNNN | NNNNNNNNNN | NNNNNNNNNN | NNAGUGCCGG | CUCGNNNNNN | NNNNNNNNNN | 120 |
| NNNNNNNNNN | NNNN | | | | | 134 |

( 2 ) INFORMATION FOR SEQ ID NO:6:

( i ) SEQUENCE CHARACTERISTICS:
        ( A ) LENGTH: 127 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

| TGATTCGCTA | GCACGTCATT | GGCTGGTAAC | ACATGACACT | ATACGAGCGA | AAAAACTACG | 60 |
| GCACCCTGGT | CCGTTAGGGA | CAACGACTAA | AGTTAGTGCC | CACGGGCTC | GTTCAGGGGG | 120 |
| GGCACGG | | | | | | 127 |

( 2 ) INFORMATION FOR SEQ ID NO:7:

( i ) SEQUENCE CHARACTERISTICS:
        ( A ) LENGTH: 115 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

| AGTCTCGCTA | GCACCTTATT | GGCTGGTAAC | ACCTGACACT | ATACGAGCGA | AAAAACTACG | 60 |
| GCACTCTGGT | CCGTACGGGC | CATGGACTTA | AGATAGTGCC | CACGGGCTC | GTTCA | 115 |

( 2 ) INFORMATION FOR SEQ ID NO:8:

( i ) SEQUENCE CHARACTERISTICS:
        ( A ) LENGTH: 127 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

```
GGACTCACTA GCACGTTGTT GGCTGGTAAC ACCCGACCCT ATACGAGCGA AAAAACTACG      60

GCACTCTGGT CCATACGGGA CTTGGACTAA AGTTAGTGCC CACGGGCTC GTTCAGGGGG      120

GGCACGG                                                                127
```

( 2 ) INFORMATION FOR SEQ ID NO:9:

( i ) SEQUENCE CHARACTERISTICS:
        ( A ) LENGTH: 127 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

```
AGACTCACTA GCGCGTTATT GGCTGGTAGC CCCTGACACT ATACAGCGAA AATACTGCGG      60

CACCCTGGTC CGTACGGGAC ATGGACATTA TGTTAGTGCC CACGGGCTC GTTCAGGGGG       120

GGCACGG                                                                127
```

( 2 ) INFORMATION FOR SEQ ID NO:10:

( i ) SEQUENCE CHARACTERISTICS:
        ( A ) LENGTH: 130 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

```
GGATATGTTG ATTCGCCCCA GCCTATAAAG TGACTCAATT CGAGGGACGC AACTACGGCA      60

CCGTCTATCT GAATCGGACG CGGAACTTGT GCCGTCTCTA CTCTAACGTT AGCGGAAAAC      120

GTGGGTTGCG                                                             130
```

( 2 ) INFORMATION FOR SEQ ID NO:11:

( i ) SEQUENCE CHARACTERISTICS:
        ( A ) LENGTH: 130 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

```
AGATGTGTCG ATTCGCCACA GCCAACAAAG CGGCCCAATT CGAGGGACGC AACTTCGGCA      60

CCGTCTATCA GAACGGGACG CGGTTCTAGT GCCGTCTCTA TCCTAACGTT AGCGGAAAAG      120

GAGGGTTGCG                                                             130
```

( 2 ) INFORMATION FOR SEQ ID NO:12:

( i ) SEQUENCE CHARACTERISTICS:
        ( A ) LENGTH: 130 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

```
AGATGTGTTG ATTCGCCTCG GCCTGTTTAG TGACCAATTT CGAGGGACGC AACTTCGGCA      60

CCGTCTACCT GCAATAGACG AGGTACTTAT GCAGGCCCTA CTTTAACGTT AGCGGGAAAC      120

GAGGGTTGCG                                                             130
```

( 2 ) INFORMATION FOR SEQ ID NO:13:

( i ) SEQUENCE CHARACTERISTICS:
        ( A ) LENGTH: 123 base pairs ( B ) TYPE: nucleic acid
( C ) STRANDEDNESS: single
( D ) TOPOLOGY: linear ( x i ) SEQUENCE DESCRIPTION: SEQ ID NO:13:

| | | | | | |
|---|---|---|---|---|---|
| AGTCTACATG | GAAGTTGTAC | TATCTAAGTG | TACTCACCAA | AGACGAGGGC | AGGAAATACG | 60
| GCACCATTGG | CTACGCAAGG | CCCAAGTGCC | CGGCGTCGTT | TCAGAAAGGA | TAACGTTAGC | 120
| CTG | | | | | | 123

( 2 ) INFORMATION FOR SEQ ID NO:14:

( i ) SEQUENCE CHARACTERISTICS:
        ( A ) LENGTH: 123 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

| | | | | | |
|---|---|---|---|---|---|
| AGGCCACTTA | GATGTCGCAC | TATCTAAGCG | TACACGCCAA | TTACGAGGGC | AGGAAATACG | 60
| GCACCTCCAG | CTACGCAAGG | CCCCAGTGCC | CTGCCTCAGT | TCGGAACGGA | TAACGTTACC | 120
| CTG | | | | | | 123

( 2 ) INFORMATION FOR SEQ ID NO:15:

( i ) SEQUENCE CHARACTERISTICS:
        ( A ) LENGTH: 121 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

| | | | | | |
|---|---|---|---|---|---|
| AGACCTCGTG | TAAGTCGTAC | TATCTAGGAG | TGCACACGAA | TACGAGGGCA | GGAAATACGG | 60
| CACCATAACT | ACGCAAGGCC | CAAGTGCCCG | GCCTTGATTC | AGAACGGATA | ACGTTAGCCT | 120
| G | | | | | | 121

( 2 ) INFORMATION FOR SEQ ID NO:16:

( i ) SEQUENCE CHARACTERISTICS:
        ( A ) LENGTH: 136 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

| | | | | | |
|---|---|---|---|---|---|
| TTATTTCGTT | CGCACCCAGT | GATCGCTCGG | GACTGGGGCC | TCCGCTAGGG | AGGACATTGC | 60
| GGCACCCAAA | CGACCACACA | GAACGTGCTA | ACGATAGTGC | CGGCTAGCAT | CCGTGAATGA | 120
| ACTGCTGCTG | CTGGCG | | | | | 136

( 2 ) INFORMATION FOR SEQ ID NO:17:

( i ) SEQUENCE CHARACTERISTICS:
        ( A ) LENGTH: 135 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

| | | | | | |
|---|---|---|---|---|---|
| AGAAGTTGTT | CGCACCCAGT | GAACGCTCGG | GACTGGGGCC | TCCGCTAGGG | AGGACATTGG | 60
| GCACCCGAAC | TATCACTCAG | AACGTGCTAT | CGATATAGCC | GGCTAGCACC | TGATTATGAA | 120
| CTGCTGCTGC | TGGCG | | | | | 135

( 2 ) INFORMATION FOR SEQ ID NO:18:

( i ) SEQUENCE CHARACTERISTICS:
        ( A ) LENGTH: 136 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

```
GGATATTGTT CGCACCCTGC GATCGCTTGG GACTGGGGCC TCCGCTAGGG AGGACATTGC      60
GGCACCCAAA CTATCACTCA GAACGTGCTA ACGATAGTGC CGGCTAGCTT CTGTAAGTGA     120
ACTGCTGCTG TTGGCG                                                    136
```

( 2 ) INFORMATION FOR SEQ ID NO:19:

( i ) SEQUENCE CHARACTERISTICS:
        ( A ) LENGTH: 137 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

```
AGACCTTAAT TCGAAAGCGT ATTCAACTTA CCATATCTCG CGCCGAGGGA AGGACCATCG      60
GCGCCAACTA CAGAGCCGTG GTTAGCGGAC TCCGCAGTGC CGGCTCGGGG AATAGGGTTC     120
TCACGAATTA CCGGCAT                                                   137
```

( 2 ) INFORMATION FOR SEQ ID NO:20:

( i ) SEQUENCE CHARACTERISTICS:
        ( A ) LENGTH: 137 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

```
AGGCCTTAAT TCGAAAGCGT ATTCGACATA CCATATTTTG CGCCGAGGGA AGATCCTTCG      60
GCACAGACTA CAGCGTCGAG GTGAGCGGCG CACACTGTGT CGGCTCGGGG AATAGGGTTC     120
TCACGAATTA CCGGCAT                                                   137
```

( 2 ) INFORMATION FOR SEQ ID NO:21:

( i ) SEQUENCE CHARACTERISTICS:
        ( A ) LENGTH: 136 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

```
AGATGTGGTT GCATAGTAGG CAGCCGGGCA CTTACGCCGA ATCGAGGGAC GAGACCGGAG      60
CACCACGATG CGCCGCGATA CCTCATTTGG GATTAGTGCC GGCTAGGAAA GTGAGTTCCT    120
TATGACCTGC CTCCAC                                                    136
```

( 2 ) INFORMATION FOR SEQ ID NO:22:

( i ) SEQUENCE CHARACTERISTICS:
        ( A ) LENGTH: 136 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

```
AGATGTGGCG GCATAGTAGG CAGCCGAGCA CTAACGCCAA ATCGAAGGAC GAGACTGCGG      60
```

```
CTCCACGATG CGCCGCGATG CCACTTTTGA GATTAGTACC GGCTGGGAAA GTGAATTCCT        120

TCTGGCCTGT CTCCAC                                                        136
```

( 2 ) INFORMATION FOR SEQ ID NO:23:

( i ) SEQUENCE CHARACTERISTICS:
        ( A ) LENGTH: 137 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

```
AGATCGATTG GAGACGCCCT GGCGTACTTT AGGTAGAAAA CTCCGACGGA AAAAACTGCG        60

GCACCGTGGG AGTAGAGGAT AGATAACAGG GCATTAGTGC CGGCCTCGCA AAGCTACCAT       120

GAGATGGAGC GATCAGG                                                      137
```

( 2 ) INFORMATION FOR SEQ ID NO:24:

( i ) SEQUENCE CHARACTERISTICS:
        ( A ) LENGTH: 137 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

```
GGTTAGATTG GAAGCGCCCC GACTTACTTT AGGTTGAAAA CTCCGACGGA AAAACTACAG        60

CACCGTGGGA GTAGAGGATG GGATATCAGG CATTAGTGCC GGCCTCGTAA AGCTACCAGG       120

ATATTGGGAC GATCAGG                                                      137
```

( 2 ) INFORMATION FOR SEQ ID NO:25:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

```
CGAGGGAAGA AAAUGCGGCA CCAGUGCCGG CUCG                                    34
```

( 2 ) INFORMATION FOR SEQ ID NO:26:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

```
ACGAGCGAAA AAACUACGGC ACUAGUGCCC ACGGGGCUCG U                            41
```

( 2 ) INFORMATION FOR SEQ ID NO:27:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

```
CGAGGGCAGG AAAUACGGCA CCAGUGCCCG GCCUUG                                  36
```

( 2 ) INFORMATION FOR SEQ ID NO:28:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:28:

```
GCUAGGGAGG ACAUUGCGGC ACCAGUGCCG GCUAGC                        36
```

(2) INFORMATION FOR SEQ ID NO:29:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:29:

```
CCGAGGGAAG AUCCUUCGGC ACAUGUGUCG GCUCGG                        36
```

(2) INFORMATION FOR SEQ ID NO:30:

(i) SEQUENCE CHARACTERISTICS:
    (A) LENGTH: 92 base pairs
    (B) TYPE: nucleic acid
    (C) STRANDEDNESS: single
    (D) TOPOLOGY: linear (xi) SEQUENCE DESCRIPTION: SEQ ID NO:30:

```
GGAACCUACG AGCGAAAAAA CUACGGCACU CUGGUCCAUA CGGGACUUGG ACUAAAGUUA    60
GUGCCCACGG GGCUCGUUCA AGGUUCUCAC GG                                 92
```

(2) INFORMATION FOR SEQ ID NO:31:

(i) SEQUENCE CHARACTERISTICS:
    (A) LENGTH: 85 base pairs
    (B) TYPE: nucleic acid
    (C) STRANDEDNESS: single
    (D) TOPOLOGY: linear (xi) SEQUENCE DESCRIPTION: SEQ ID NO:31:

```
ACGAGCGAAA AAACUACGGC ACUCUGGUCC AUACGGGACU UGGACUAAAG UUAGUGCCCA    60
CGGGGCUCGU UCAAGGUUCU CACGG                                         85
```

(2) INFORMATION FOR SEQ ID NO:32:

(i) SEQUENCE CHARACTERISTICS:
    (A) LENGTH: 112 base pairs
    (B) TYPE: nucleic acid
    (C) STRANDEDNESS: single
    (D) TOPOLOGY: linear (xi) SEQUENCE DESCRIPTION: SEQ ID NO:32:

```
GGAACACTAT CCGACTGGCA CCNNNNNNNN NNNNNNNNNN NNNNNNNNNN NNNNNNNNNN    60
NNNNNNNNNN NNNNNNNNNN NNNNNNNNNN NNNNCCTTGG TCATTAGGAT CG           112
```

(2) INFORMATION FOR SEQ ID NO:33:

(i) SEQUENCE CHARACTERISTICS:
    (A) LENGTH: 156 base pairs
    (B) TYPE: nucleic acid
    (C) STRANDEDNESS: single
    (D) TOPOLOGY: linear (xi) SEQUENCE DESCRIPTION: SEQ ID NO:33:

-continued

```
GGAGGCACCA CGGTCGGATC CNNNNNNNNN NNNGGAACAC TATCCGACTG GCAAAGACCA      60
TAGGCTCGGG TTGCCAGAGG TTCCACACTT TCATCGAAAA GCCTATGCTA GGCAATGACA     120
TGGACTNNNN NNNNNNNNCC TTGGTCATTA GGATCG                               156
```

( 2 ) INFORMATION FOR SEQ ID NO:34:

( i ) SEQUENCE CHARACTERISTICS:
        ( A ) LENGTH: 156 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:34:

```
GGAGGCACCA CGGTCGGATC CGGTTTATTA TCATGAGCCC GACTCGACGG GCACTGTACA      60
TAAGCTTCGG ATGCCATAGT TTAGACACTA TGGACGTAAA GCCCATGCTA GGCAAAGACA     120
TTGACTGCAT GAGCGCCGCC TTGGTCATTA GGATCG                               156
```

( 2 ) INFORMATION FOR SEQ ID NO:35:

( i ) SEQUENCE CHARACTERISTICS:
        ( A ) LENGTH: 117 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:35:

```
NNNNNNNNNN NNGGAACACT ATCCGACTGG CACCGACCAT AGGCTCGGGT TGCCAGAGGT      60
TCCACACTTT CATCGAAAAG CCTATGCTAG GCAATGACAT GGACTNNNNN NNNNNNN       117
```

( 2 ) INFORMATION FOR SEQ ID NO:36:

( i ) SEQUENCE CHARACTERISTICS:
        ( A ) LENGTH: 117 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:36:

```
TTGCGGTGGG ANGGACCACA TGCCGCCTGG CACCGACCAT AGGCTCGGGT TGCCAGAGGT      60
TCCACAGTTT CATCGAAAAG CCTATGCTAG GAGGTTACCT AGACTTAGGG GTTCACT       117
```

( 2 ) INFORMATION FOR SEQ ID NO:37:

( i ) SEQUENCE CHARACTERISTICS:
        ( A ) LENGTH: 117 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:37:

```
ATTTCGCGAT GGGGAGCACA TAGCAACTGG CACCGACCAT AGGCTCGGGT TGCAAGAGGT      60
TCCACACTTT CATCGAAAAG CCTATGCTAG GCAATGACAT GGACTNNNNN NNNNNNN       117
```

( 2 ) INFORMATION FOR SEQ ID NO:38:

( i ) SEQUENCE CHARACTERISTICS:
        ( A ) LENGTH: 117 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:38:

```
TCTTCGGAGG CCGTTACAGA CACACACTGG CACCGACCAT AGGCTCGGGT TGTGTGAGGT      60
```

TGCCCATGTT CATCGAAAAG CCTATGCTAC CCACTGACAT GGACTTTATC CACAAGT   117

( 2 ) INFORMATION FOR SEQ ID NO:39:

( i ) SEQUENCE CHARACTERISTICS:
        ( A ) LENGTH: 117 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:39:

CAGTTATTCT GCGTAACACA TTCTGACTGA CACCGACCAT AGGCTCGGGT TGCCCTAGTT   60

GCCACACTTT CAACGAAAAG CCTATGCTAA CCTATGACGT GGACTCCGGC ATGNNNN   117

( 2 ) INFORMATION FOR SEQ ID NO:40:

( i ) SEQUENCE CHARACTERISTICS:
        ( A ) LENGTH: 117 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:40:

CAAAGGTCCT ACGGAATACA CTCTAACTGA CACCGACCAT AGGCTCGGGT CTCCAAAGGT   60

GCCACATTTT CAGCGAAAAG CCTATGCTAT CCAATGGCAT GAAGTATCAC GTCTACT   117

( 2 ) INFORMATION FOR SEQ ID NO:41:

( i ) SEQUENCE CHARACTERISTICS:
        ( A ) LENGTH: 117 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:41:

NNCGCATCGT GCTGAAGACA TTCCGACTTC GACCGACCAT AGGCTCGGGT TCCCAAAGTT   60

GTCTCACATT CTTTGAAAAG CCTATGCTAC CTAGTGACAA GGATTACGCC CGCTGAG   117

( 2 ) INFORMATION FOR SEQ ID NO:42:

( i ) SEQUENCE CHARACTERISTICS:
        ( A ) LENGTH: 117 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:42:

ACGTCCGCCA ACGGTGGACA TTCTGACGGG CACCGACCAT AGGCTCGGGT TGGCCGCGGT   60

TTCATACTTT CATTGAAAAG CCTATGCCAG GCAGTGACAT GAACTTTGAG GTAAAGT   117

( 2 ) INFORMATION FOR SEQ ID NO:43:

( i ) SEQUENCE CHARACTERISTICS:
        ( A ) LENGTH: 117 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:43:

CCCTGTTAAA GAGGAACACA TTCCGACTGC TACCGACCAT AGGCTCGGGT TCGTTGAGGT   60

GCCACACATG CATTGACAAG CTTATGCTAG GGGTTGCCAT GGACTNNNNN NNNNNNN   117

( 2 ) INFORMATION FOR SEQ ID NO:44:

( i ) SEQUENCE CHARACTERISTICS:
    ( A ) LENGTH: 117 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:44:

```
CAAGAACCGG CCGAAAAACA TTCCAACTGG TACCGACCAT AGGCTCGGGT TCCCAGACAT      60
TACACATTTT CTTTGAAAAG CCTATGATAT CCGCTGACCG TGACCGCTAG CGGCATC       117
```

( 2 ) INFORMATION FOR SEQ ID NO:45:

( i ) SEQUENCE CHARACTERISTICS:
    ( A ) LENGTH: 117 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:45:

```
TGGACTTTTC ACGGAACATG TTCCGATTGG CACCGACCAT AGGCTCGGCT TTCCAGAGGT      60
GCCACAACTT CATTGAAAAG CCTATGCTAG CCAATGACCT GGACCATCAC AAAGGTT       117
```

( 2 ) INFORMATION FOR SEQ ID NO:46:

( i ) SEQUENCE CHARACTERISTICS:
    ( A ) LENGTH: 117 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:46:

```
CTTCATTAAA GGGGAAAACA TTCCGACTGG GACCGACCAT AGGCTCGGTT TTTCAGAAGG      60
CACTCTGTTG CGTCGACAAG CCTATGCTGG ACCATGACCT GGACTATTTG CCCAGAT       117
```

( 2 ) INFORMATION FOR SEQ ID NO:47:

( i ) SEQUENCE CHARACTERISTICS:
    ( A ) LENGTH: 117 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:47:

```
TGATGAGAGC TACGAACACA CACCGACTGG CACCGACCAT AGGCTCGGTT TGCCTCAGAT      60
TCTTACCTTT CTTTGAAAAG CCTATGCTTG CTAATGACCT GGATTTGAGA ACANNNN       117
```

( 2 ) INFORMATION FOR SEQ ID NO:48:

( i ) SEQUENCE CHARACTERISTICS:
    ( A ) LENGTH: 117 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:48:

```
GACACAAAGC AGGCAACAAA TTCCGACTGG TACCGACCAT AGGCTCGGTT TGCCCGAGCT      60
TCCACACTTT CATCGAAAAG CCTATGTTAG CTAATGACAG GGAGGACTCG ATGTGGT       117
```

( 2 ) INFORMATION FOR SEQ ID NO:49:

( i ) SEQUENCE CHARACTERISTICS:
    ( A ) LENGTH: 117 base pairs
    ( B ) TYPE: nucleic acid
    ( C ) STRANDEDNESS: single ( D ) TOPOLOGY: linear ( x i ) SEQUENCE DESCRIPTION: SEQ ID NO:49:

CCGAGCGGTC GGGGACGACA TTCCGTCTGG CACCGACCAT AGGCTCGGTT CTCCAGAGCT 60

TCCAAACCTT CTTGGAAAAG CCTATGCTGG GCAATGACAT GGACTNNNNN NNNNNNN 117

( 2 ) INFORMATION FOR SEQ ID NO:50:

( i ) SEQUENCE CHARACTERISTICS:
        ( A ) LENGTH: 117 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:50:

AGTGTCATAT TAGGGACACA GTCCGTATCG CACCGATCAT AGGCTCGGTT TGGCACGCGT 60

GCCACACTTG CAACGACAAG CCTATGGTAG TCCATAACCT GGACTACAAA CCCGATT 117

( 2 ) INFORMATION FOR SEQ ID NO:51:

( i ) SEQUENCE CHARACTERISTICS:
        ( A ) LENGTH: 117 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:51:

CCCTAGTGGA TAGGAACACA TTACGCCTGG CACCGACCAT AGGCTCGGTT GACCAGCGTT 60

TCCACACTTT CATCGAAAAG CCTATGCTTG CCATTGACAT GGACTCACGC ATTGCAT 117

( 2 ) INFORMATION FOR SEQ ID NO:52:

( i ) SEQUENCE CHARACTERISTICS:
        ( A ) LENGTH: 117 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:52:

GTGCCGACTT ACGGTTCACA TTCAAACTGG CACCGACCAT AGGCTCGGTT TGCCTAACGT 60

TTCAAACTTT CATCGAAAAG CCTATGCTGG GCAACGGTTA GGGTTTCGCA CGGCGAT 117

( 2 ) INFORMATION FOR SEQ ID NO:53:

( i ) SEQUENCE CHARACTERISTICS:
        ( A ) LENGTH: 117 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:53:

CTGCACAGGT AGGGAACGCA TTTCGACTCG CACCGACCAT AGGCTCGGTC AGCGAGTTGC 60

GCCCCAATTT CAACGAAAAG CCTATGCTAG GTAATGCCAT GGACTGGTTC GTATCAT 117

( 2 ) INFORMATION FOR SEQ ID NO:54:

( i ) SEQUENCE CHARACTERISTICS:
        ( A ) LENGTH: 117 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:54:

GACGGAACCG TTTTAACACG TTCCGACCGG CACCGACCAT AGGCTCGGTT TGCCAGAGCT 60

TCACAACTTT CATCGAAAAG CCTATGAAAT GTAACGACAA GGACTACTCG ACCAGCA 117

(2) INFORMATION FOR SEQ ID NO:55:

(i) SEQUENCE CHARACTERISTICS:
        (A) LENGTH: 117 base pairs
        (B) TYPE: nucleic acid
        (C) STRANDEDNESS: single
        (D) TOPOLOGY: linear (x i) SEQUENCE DESCRIPTION: SEQ ID NO:55:

GGGTCGTGGC GCGGAACAAA TTCCCACAGG CACCGACCAT AGGCTCGGTT TGCCTGTTGC 60

TCCACACCTT CATCGAAAAG CCTATGCCCG GCAATCACTT GGCCTTTGGA CGTCATT 117

(2) INFORMATION FOR SEQ ID NO:56:

(i) SEQUENCE CHARACTERISTICS:
        (A) LENGTH: 117 base pairs
        (B) TYPE: nucleic acid
        (C) STRANDEDNESS: single
        (D) TOPOLOGY: linear (x i) SEQUENCE DESCRIPTION: SEQ ID NO:56:

GCTCTGTTCG GTTCAACAAA TTCACACTGG CAAAGACCAT AGGCTCGGTT TGCCAGAGGT 60

GCCACAGTTC ACTCGAAAAG CCTATGATCG CCAATGACAT GTACCTCACG CTAGGCA 117

(2) INFORMATION FOR SEQ ID NO:57:

(i) SEQUENCE CHARACTERISTICS:
        (A) LENGTH: 117 base pairs
        (B) TYPE: nucleic acid
        (C) STRANDEDNESS: single
        (D) TOPOLOGY: linear (x i) SEQUENCE DESCRIPTION: SEQ ID NO:57:

ACACTATGTA CTGGAAAACG TTCGGACACA CACCGACTAT AGGCTCGGTT TGCCATTGGT 60

GCCACAGTTG CAGCGAAAAG CCTATGCGGG GCCATGACAC GTACTGCCCA GTAACGT 117

(2) INFORMATION FOR SEQ ID NO:58:

(i) SEQUENCE CHARACTERISTICS:
        (A) LENGTH: 117 base pairs
        (B) TYPE: nucleic acid
        (C) STRANDEDNESS: single
        (D) TOPOLOGY: linear (x i) SEQUENCE DESCRIPTION: SEQ ID NO:58:

TGCTACTGTT ATGTAACACA TTCCGACTGC GACCGACCAT AGGCTCGGTT TTCCAGACGT 60

TCGTCACTTG CTTCGACAAG CCTATGAAAT TCAATGACAT GGCCTGGCTA GGCGCGA 117

(2) INFORMATION FOR SEQ ID NO:59:

(i) SEQUENCE CHARACTERISTICS:
        (A) LENGTH: 117 base pairs
        (B) TYPE: nucleic acid
        (C) STRANDEDNESS: single
        (D) TOPOLOGY: linear (x i) SEQUENCE DESCRIPTION: SEQ ID NO:59:

TCTATGGCCG TGCAAACACA CTACGTCTGG CCCCGACCAT AGGCTCGGGT TGCCAGCGTT 60

TGCAAGGTTT CATCGAAAAG CCTATGCGAT CTAATGACAT GGACCGGAAG GCCCAAT 117

(2) INFORMATION FOR SEQ ID NO:60:

( i ) SEQUENCE CHARACTERISTICS:
    ( A ) LENGTH: 117 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:60:

CTAAATTTGG TTGAAACACA TGCAGACTGG CCCCGACCAT AGGCTCGGGT TGTCAGAGGT 60

GCTTCACGTT CCTCGAAAAG CCTATGTGAT GGAATGACAT TGACTGAGGG ATGCGGT 117

( 2 ) INFORMATION FOR SEQ ID NO:61:

( i ) SEQUENCE CHARACTERISTICS:
    ( A ) LENGTH: 117 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:61:

GCNGAGGGCT CCGGTACACA TGCAGACTGG TCCCGACCAT AGGCTCGGGT TACCAGACCT 60

TCAACTACTT CTTCGAAAAG CCTATGCCGG TCAAGGCCAT GAACGCTCAA TCAGTGT 117

( 2 ) INFORMATION FOR SEQ ID NO:62:

( i ) SEQUENCE CHARACTERISTICS:
    ( A ) LENGTH: 117 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:62:

TGTCCGAACG ACGTATGCCA TTCGTCTGG CCCCGACCAT AGGCTCGGAT TACCATTCGT 60

TACACACTTT CATCGAAAAG CCTATGCTGT TCAATGGCCC GGACTTCAGT AGATGGT 117

( 2 ) INFORMATION FOR SEQ ID NO:63:

( i ) SEQUENCE CHARACTERISTICS:
    ( A ) LENGTH: 117 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:63:

CGGAATTACA CTGGATCACA TCCCGACTGG CCCCGACCAT AGGCTCGGGT TGCCAGTGCT 60

TACACCCTTT CACCGAAAAG GCTATGCTAG GCCATGCCAT TAACTNNNNN NNNNNNN 117

( 2 ) INFORMATION FOR SEQ ID NO:64:

( i ) SEQUENCE CHARACTERISTICS:
    ( A ) LENGTH: 117 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:64:

GGTTTATTAT CATGAGCCCG ACTCGACGGG CACTGTACAT AAGCTTCGGA TGCCATAGTT 60

TAGACACTAT GGACGTAAAG CCCATGCTAG GCAAAGACAT TGACTGCATG AGCGCCG 117

( 2 ) INFORMATION FOR SEQ ID NO:65:

( i ) SEQUENCE CHARACTERISTICS:
    ( A ) LENGTH: 117 base pairs
    ( B ) TYPE: nucleic acid
    ( C ) STRANDEDNESS: single ( D ) TOPOLOGY: linear ( x i ) SEQUENCE DESCRIPTION: SEQ ID NO:65:

GGTTTATCAT GTTTTAATCC CTACGCGGTC ACATTTGAAT AACCGGGGAA TTACAGAGTG 60

TAAACACTAT GAACGTAAAG ACCATGCGAA GCTATGACAC TGACTGCATG GTCGCGG 117

( 2 ) INFORMATION FOR SEQ ID NO:66:

( i ) SEQUENCE CHARACTERISTICS:
        ( A ) LENGTH: 117 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:66:

GGGGTTTTTG TCGCGGACCC TCGCGACGTT CACTGTACAT AAGCTTCGGA TGCCGTAGAG 60

TAAACACTGC GGACGTAAAG CTCATGTTGG GTATTAAACC AAACAACATT AGCCCCG 117

( 2 ) INFORMATION FOR SEQ ID NO:67:

( i ) SEQUENCE CHARACTERISTICS:
        ( A ) LENGTH: 117 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:67:

AGCTTCTCAT CAGTCGGTCC CACTCCACCG ACATTTACGT AAGCTTTGGA TGCCATAGTA 60

AAAACACTAT GGACGTAAAG CGCAACGTAG CCCAAGATAT TGACAGTTTG AGCGCCG 117

( 2 ) INFORMATION FOR SEQ ID NO:68:

( i ) SEQUENCE CHARACTERISTICS:
        ( A ) LENGTH: 117 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:68:

GTTTTATGTT CAAGTGCCCG AAACGGCCGG CACTGTACAT AACCCTCGGA TGCAATAGTC 60

TAGACGCTAT TGGTGTAAAG CCCATATTAG ACAAGGACCT TGTCTTCATG AGCGCCG 117

( 2 ) INFORMATION FOR SEQ ID NO:69:

( i ) SEQUENCE CHARACTERISTICS:
        ( A ) LENGTH: 117 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:69:

GTTTTAGCAT TGTGAGCCCC GCTCCACGGT CACTCTGAAG ATGCTTCGGA TGCCATAGTT 60

CGCACACTAT GGACGTAAAG ATTGTTCGAG TCACAGACAG TAGCTGCACA ATCGCCG 117

( 2 ) INFORMATION FOR SEQ ID NO:70:

( i ) SEQUENCE CHARACTERISTICS:
        ( A ) LENGTH: 117 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:70:

GGTTGAAATA AGCGTTAGGC CTACTTGACG CTCAGTAGGC AATCACCGGA TGCCGTAGTT 60

TATACACTAT GGACGTAAAG GTCATGCTGT TCTAAGACAT TGTCTGCATG ACCGCCG          117

( 2 ) INFORMATION FOR SEQ ID NO:71:

( i ) SEQUENCE CHARACTERISTICS:
        ( A ) LENGTH: 117 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:71:

GAAATTTGT GTGCAGACAC TACTCTCCTG CACCGTTTAA AAGCTTCGGA TGCCATAGGT          60

TAAAAACTAT GGACGTAAAG CGCATGATCG GTAAACACAG TTACTGCATG ATCGCCG          117

( 2 ) INFORMATION FOR SEQ ID NO:72:

( i ) SEQUENCE CHARACTERISTICS:
        ( A ) LENGTH: 117 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:72:

GGTTTATCAT GTTTAATCC CTACGCGGGT CACATTTGAA TACCGGGGAA TTACAGAGTG          60

TAAACACTAT GAACGTAAAG ACCATGCGAA GCTATGACAC TGACTGCATG GTCGCGG          117

( 2 ) INFORMATION FOR SEQ ID NO:73:

( i ) SEQUENCE CHARACTERISTICS:
        ( A ) LENGTH: 117 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:73:

GGTTTATCAT GTTTAATCC CTACGCGGGT CACATTTGAA TACCGGGGAA TTACAGAGTG          60

TAAACACTAT GAACGTAAAG ACCATGCGAA GCTATGACAC TGACTGCATG GTCGCGG          117

( 2 ) INFORMATION FOR SEQ ID NO:74:

( i ) SEQUENCE CHARACTERISTICS:
        ( A ) LENGTH: 117 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:74:

GGTTGAAAAA CATGAGCCAG TCTCGACGAG ACTTCTCGTT TCTAATCGGA TGCCATAGTT          60

AAGATACTAT GGACGTAAAG CGCTCGGTAG CTAAGAACAG TGTTTGCCAG CGCGCCG          117

( 2 ) INFORMATION FOR SEQ ID NO:75:

( i ) SEQUENCE CHARACTERISTICS:
        ( A ) LENGTH: 117 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:75:

GGATTGTTAT ACCTTGGCCT GGATCCTAGC CACTGTAGCT ATCATCCGGA TGCCAGAGTT          60

TAGCCACTCT GGACGTAAAG CTCATGTTAA GAATAGACAT TGAATGCATG AGCGCCC          117

( 2 ) INFORMATION FOR SEQ ID NO:76:

(i) SEQUENCE CHARACTERISTICS:
  (A) LENGTH: 117 base pairs
  (B) TYPE: nucleic acid
  (C) STRANDEDNESS: single
  (D) TOPOLOGY: linear (xi) SEQUENCE DESCRIPTION: SEQ ID NO:76:

| GATGCATTAT | CTCGCGTGCG | TGTAGACGGG | GTCGACACGC | AAGCTTCGGA | TGCCATAGAT | 60 |
| TAGATACTAT | GGACGTAAAG | CTCATGTTAG | TCAAAAACAC | TGGCTCCATG | AGCGCCG | 117 |

(2) INFORMATION FOR SEQ ID NO:77:

(i) SEQUENCE CHARACTERISTICS:
  (A) LENGTH: 117 base pairs
  (B) TYPE: nucleic acid
  (C) STRANDEDNESS: single
  (D) TOPOLOGY: linear (xi) SEQUENCE DESCRIPTION: SEQ ID NO:77:

| GGAAAATCAT | ATAAGTCCCG | TCGCCCCGCG | AACTTTACGT | AAGATTCGGA | TGCCATAGTT | 60 |
| TATCCACTAT | GGGTGTAAAG | GTCATGCTAT | ACCAACACAT | TTATGGCATG | ATCGCCG | 117 |

(2) INFORMATION FOR SEQ ID NO:78:

(i) SEQUENCE CHARACTERISTICS:
  (A) LENGTH: 117 base pairs
  (B) TYPE: nucleic acid
  (C) STRANDEDNESS: single
  (D) TOPOLOGY: linear (xi) SEQUENCE DESCRIPTION: SEQ ID NO:78:

| GAAATTTGT | GTGCAGACAC | TACCCTCCTG | CACCGTTAAA | AAGCTTCGGA | TGCCATAGGT | 60 |
| TAAAAACTAT | GGACGTAAAG | CGCATGATCG | GTAAACACAG | TTACTGCATG | TGCGCCG | 117 |

(2) INFORMATION FOR SEQ ID NO:79:

(i) SEQUENCE CHARACTERISTICS:
  (A) LENGTH: 117 base pairs
  (B) TYPE: nucleic acid
  (C) STRANDEDNESS: single
  (D) TOPOLOGY: linear (xi) SEQUENCE DESCRIPTION: SEQ ID NO:79:

| GGTGTATTAG | CTTGAGTCCA | ACTCCACGAG | CACTATGAAT | AATCTTCGGA | TGCCATCGTT | 60 |
| TCAACACGAT | GGACGTAAAG | CCCACTGTTG | GCAAATACAT | TGACTGCAGG | TGCGCCG | 117 |

(2) INFORMATION FOR SEQ ID NO:80:

(i) SEQUENCE CHARACTERISTICS:
  (A) LENGTH: 117 base pairs
  (B) TYPE: nucleic acid
  (C) STRANDEDNESS: single
  (D) TOPOLOGY: linear (xi) SEQUENCE DESCRIPTION: SEQ ID NO:80:

| GATGCATTAT | CTCGCGTGCG | TGTAGACGGG | GATCGACACC | AAGCTTCGGA | TGCCATAGAT | 60 |
| TAGACACTAT | GGACGTAAAG | CGCATGTTAG | TAGAAATCAA | CTGCAGCACG | ACCGCCG | 117 |

(2) INFORMATION FOR SEQ ID NO:81:

(i) SEQUENCE CHARACTERISTICS:
  (A) LENGTH: 117 base pairs
  (B) TYPE: nucleic acid
  (C) STRANDEDNESS: single ( D ) TOPOLOGY: linear ( x i ) SEQUENCE DESCRIPTION: SEQ ID NO:81:

| GAAATTTTGT | GTGCAGACAC | TACTCTCCTG | CACCGTTTAA | AAGCTTCGGA | TGCCATAGGT | 60 |
| TAAAAACTAT | GGACGTAAAG | CGCATGATCG | GTAAACACAG | TTACTGCATG | TGCGCCG | 117 |

( 2 ) INFORMATION FOR SEQ ID NO:82:

( i ) SEQUENCE CHARACTERISTICS:
       ( A ) LENGTH: 117 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:82:

| GATTTATTCA | TATGAGCCGG | GTTGAAAGTA | TAAAGTACTT | TAGCTTCGGC | TGCCAAAGTT | 60 |
| TATAAACTTT | GGACGTAAAG | CTCCTGCTTG | GCAAATACAA | AAGCTGCACG | AGCGCCA | 117 |

( 2 ) INFORMATION FOR SEQ ID NO:83:

( i ) SEQUENCE CHARACTERISTICS:
       ( A ) LENGTH: 117 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:83:

| GGTTACTTAA | TGCGACCAAC | CTACGGGGCA | CTGTCTACAT | AAGTTTCGGA | TGCCATAGTG | 60 |
| ATGCAACTAT | GGACGTAAAG | CCCATGCCAG | ACTAAAACAT | TGTCTGCATG | CGCGCCG | 117 |

( 2 ) INFORMATION FOR SEQ ID NO:84:

( i ) SEQUENCE CHARACTERISTICS:
       ( A ) LENGTH: 117 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:84:

| GGAGTCTTTT | CATGAGTCCG | ACTCTCCACT | CATTGTTCAT | AAGCTCCGGA | TGCCATAGCT | 60 |
| CAAAAACTAT | GGACGTAAAG | CCCATGCTAA | GCTCTCAAGT | TGACTGCATG | AGCGCCG | 117 |

( 2 ) INFORMATION FOR SEQ ID NO:85:

( i ) SEQUENCE CHARACTERISTICS:
       ( A ) LENGTH: 117 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:85:

| GATTTATTCA | TATGAGCCGG | GTTGAAAGTA | TAAAGTACTT | TAGCTTCGGC | TGCCAAAGTT | 60 |
| TATAAACTTT | GGACGTAAAG | CCCATGTTAG | GTAAGATTAT | TAACAGCATG | TGCGCCG | 117 |

( 2 ) INFORMATION FOR SEQ ID NO:86:

( i ) SEQUENCE CHARACTERISTICS:
       ( A ) LENGTH: 117 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:86:

| GCTTTATTCT | CTCTTGCCCT | GATCCACGGG | CAGGATACGA | GGGATGCGGA | TGCCATATTT | 60 |

```
TAAAAAGTAT GGACGTAAAG CCCATGATAA GCAAAGATTG TCACATCATG TGCGCCG        117
```

( 2 ) INFORMATION FOR SEQ ID NO:87:

( i ) SEQUENCE CHARACTERISTICS:
        ( A ) LENGTH: 99 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:87:

```
GGAACCAAGG CGGAUCCGGA UGAGAUCCGG AUGCCAUAGU AAAAACACUA UGGACGUAAA     60
GCUCAGGCUG AAGACACAGC CUGAGCGCCG CCUUGGUUC                             99
```

( 2 ) INFORMATION FOR SEQ ID NO:88:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:88:

```
GGAACACUAU GGACGUAAAG CUCAGGCUGA A                                    31
```

( 2 ) INFORMATION FOR SEQ ID NO:89:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:89:

```
GGAAACAGCC UGAGCGCCGC CUUGGUUCGA AAGAACCAAG GCGGAUCCGG AUGAGAUCCG     60
GAUGCCAUAG UAA                                                        73
```

( 2 ) INFORMATION FOR SEQ ID NO:90:

( i ) SEQUENCE CHARACTERISTICS:
        ( A ) LENGTH: 110 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:90:

```
GGAACACUAU CCGAUGGCAC CGACCAUAGG CUCGGGUUGC CAGAGGUUCC ACACUUUCAU     60
CGAAAAGCCU AUGCUAGGCA AUGACAUGGA CUCCUUGGUC AUUAGGAUCG                110
```

( 2 ) INFORMATION FOR SEQ ID NO:91:

( i ) SEQUENCE CHARACTERISTICS:
        ( A ) LENGTH: 155 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:91:

```
GGAGGCACCA CGGCUGGAUC CGGUUUAUUA UCAUGAGCCC GACUCGGGCA GCACUGUACA     60
UAAGCUCGGA UGCCAUAGUU UAGACACUAU GGACGUAAAG CCCAUGCUAG GCAAAGACAU    120
UGACUGCAUG AGCGCCGCCU UGGUCAUUAG GAUCG                               155
```

Other embodiments are within the following claims.

What is claimed is:

1. A method for producing a self-modifying RNA molecule which binds a first ligand and carries out a chemical reaction modifying said self-modifying RNA molecule, comprising the steps of:
   a) providing a first population of RNA molecules comprising RNA molecules having a first region of random sequence;
   b) contacting said first population of RNA molecules with said first ligand;
   c) isolating a first ligand-binding subpopulation of said first population of RNA molecules by partitioning RNA molecules in said first population which specifically bind said first ligand from those which do not;
   d) amplifying said first ligand-binding subpopulation in vitro;
   e) identifying a first ligand binding RNA sequence present in said amplified first ligand-binding subpopulation;
   f) preparing a second population of RNA molecules comprising RNA molecules comprising said first ligand binding sequence and a second region of random sequence;
   g) contacting said second population of RNA molecules with a second ligand which binds said first ligand binding sequence, said contacting occurring under conditions which allow said second ligand to participate in a chemical reaction which modifies an RNA molecule in said second population; and
   h) isolating a subpopulation of said self-modifying RNA molecules from said population of RNA molecules by partitioning RNA molecules which have been modified in step g) from those which have not been modified.

2. The method of claim 1 wherein said first ligand is ATP.

3. The method of claim 1 wherein said first ligand is biotin.

4. The method of claim 1 wherein said self-modifying RNA molecule transfer a phosphate from a nucleotide triphosphate to said self-modifying RNA molecule.

5. The method of claim 4 wherein said transfer is to the 5'-hydroxyl of said self-modifying RNA molecule.

6. The method of claim 4 wherein said transfer is to an internal 2'-hydroxyl of said self-modifying RNA molecule.

7. The method of claim 1 wherein said self-modifying RNA molecule transfers a phosphate from a nucleotide triphosphate to a nucleic acid other than said self-modifying RNA molecule.

8. The method of claim 7 wherein said nucleic acid is a ribonucleic acid.

9. The method of claim 1 wherein said first and second ligands are the same.

10. The method of claim 1 wherein said self-modifying RNA molecule carries out N-alkylation.

11. The method of claim 10 wherein said self-modifying RNA molecule carries out N-alkylation of said self-modifying RNA molecule.

12. The method of claim 10 wherein said self-modifying RNA molecule carries out N-alkylation of a nucleic acid other than said self-modifying RNA molecule.

13. A self-modifying RNA molecule which transfers a phosphate from a nucleotide triphosphate to said self-modifying RNA molecule, said self-modifying RNA molecule being produced by the method of claim 1.

14. The self-modifying RNA molecule of claim 13 wherein said transfer is to the 5'-hydroxyl of said self-modifying RNA molecule.

15. The self-modifying RNA molecule of claim 13 wherein said transfer is to an internal 2'-hydroxyl of said self-modifying RNA molecule.

16. A self-modifying RNA molecule which transfers a phosphate from a nucleotide triphosphate to a nucleic acid other than said self-modifying RNA molecule said self-modifying RNA molecule being produced by the method of claim 1.

17. The self-modifying RNA molecule of claim 16 wherein said nucleic acid is a ribonucleic acid.

18. A self-modifying RNA molecule which carries out N-alkylation of said self-modifying RNA, said self-modifying RNA molecule being produced by the method of claim 1.

19. The self-modifying RNA molecule of claim 18 wherein said self-modifying RNA molecule caries out N-alkylation of a nucleic acid other than said self-modifying RNA molecule.

* * * * *

UNITED STATES PATENT AND TRADEMARK OFFICE
CERTIFICATE OF CORRECTION

PATENT NO. 5,688,670
DATED      November 18, 1997
INVENTORS  Jack W. Szostak, Jon R. Lorsch, and Charles Wilson It is certified that error appears in the above-identified patent and that said Letters Patent is hereby corrected as shown below:

At col 1, line 20, replace "Bennet" with --Benner--;

At col 8, line 21, replace ">20%" with --<20%--;

At col 9, line 60, replace "BBS-5" with BB8-5--;

At col 10, line 39, replace "nucleotides 5" with --nucleotides--;

At col 13, line 62, replace "61" with --261--;

At col 13, line 63, replace "Appl., 28" with --Appl., 2:28--;

At col 16, line 3, replace "ATP-γ-S" with --ATP-α-S--;

At col 16, line 63, replace "~4x10-4 min-1" with --~4x10$^{-4}$ min$^{-1}$;

At col 18, line 52, replace "≥90%" with -- >90% --;

UNITED STATES PATENT AND TRADEMARK OFFICE
CERTIFICATE OF CORRECTION

PATENT NO. : 5,688,670
DATED : November 18, 1997
INVENTOR(S) : Jack W. Szostak, Jon R. Lorsch, and Charles Wilson It is certified that error appears in the above-indentified patent and that said Letters Patent is hereby corrected as shown below:

At col. 21, line 51, replace "specstreptncrease" with --specific increase--.

Signed and Sealed this

Sixteenth Day of November, 1999

Attest:

Q. TODD DICKINSON

Attesting Officer

Acting Commissioner of Patents and Trademarks